US012661495B2

(12) United States Patent
Wallin et al.

(10) Patent No.: US 12,661,495 B2
(45) Date of Patent: Jun. 23, 2026

(54) INTRAVASCULAR BLOOD PUMP SYSTEMS AND METHODS OF USE AND CONTROL THEREOF

(71) Applicant: Shifamed Holdings, LLC, Campbell, CA (US)

(72) Inventors: Joshua Wallin, San Jose, CA (US); Adnan Merchant, Fremont, CA (US); Gerald Lyons, Saratoga, CA (US); Bertold Engler, Munich (DE); Tom Peach, Milan (IT); Andrea Besana, Campbell, CA (US); James Luther, Minneapolis, MN (US)

(73) Assignee: Supira Medical, Inc., Los Gatos, CA (US)

( * ) Notice: Subject to any disclaimer, the term of this patent is extended or adjusted under 35 U.S.C. 154(b) by 290 days.

(21) Appl. No.: 18/345,285

(22) Filed: Jun. 30, 2023

(65) Prior Publication Data

US 2024/0173540 A1 May 30, 2024

Related U.S. Application Data

(63) Continuation of application No. 17/033,482, filed on Sep. 25, 2020, now Pat. No. 11,724,089.

(Continued)

(51) Int. Cl.
| | |
|---|---|
| *A61M 60/117* | (2021.01) |
| *A61M 1/36* | (2006.01) |
| *A61M 60/109* | (2021.01) |
| *A61M 60/126* | (2021.01) |
| *A61M 60/13* | (2021.01) |

(Continued)

(52) U.S. Cl.
CPC .... *A61M 60/117* (2021.01); *A61M 1/362227* (2022.05); *A61M 1/36224* (2022.05); *A61M 1/362265* (2022.05); *A61M 60/109* (2021.01); *A61M 60/126* (2021.01); *A61M 60/237* (2021.01); *A61M 60/279* (2021.01); *A61M 60/531* (2021.01); *A61M 60/585* (2021.01); *A61M 60/808* (2021.01); *A61M 60/81* (2021.01); *A61M 60/847* (2021.01); *A61M 60/851* (2021.01); *A61M 60/857* (2021.01); *A61M 60/865* (2021.01); *A61M 1/36225* (2022.05)

(58) Field of Classification Search
CPC ...................... A61M 1/362227; A61M 60/847
See application file for complete search history.

(56) References Cited

U.S. PATENT DOCUMENTS

| | | |
|---|---|---|
| 4,625,712 A | 12/1986 | Wampler |
| 4,753,221 A | 6/1988 | Kensey et al. |

(Continued)

FOREIGN PATENT DOCUMENTS

| | | |
|---|---|---|
| CA | 3014105 A1 | 8/2017 |
| EP | 3131599 A1 | 2/2017 |

(Continued)

*Primary Examiner* — Brian T Gedeon
(74) *Attorney, Agent, or Firm* — Shay Glenn LLP

(57) ABSTRACT

Intravascular blood pumps and methods of use. The blood pump include a pump portion that includes a collapsible blood conduit defining a blood flow lumen between an inflow and an outflow. The pump portion includes a distal collapsible impeller axially spaced from a proximal collapsible impeller, at least a portion of each of the distal and proximal collapsible impellers disposed between the inflow and the outflow.

16 Claims, 39 Drawing Sheets

Related U.S. Application Data

(60) Provisional application No. 62/905,746, filed on Sep. 25, 2019, provisional application No. 62/905,802, filed on Sep. 25, 2019.

(51) Int. Cl.

| | | |
|---|---|---|
| *A61M 60/237* | (2021.01) |
| *A61M 60/279* | (2021.01) |
| *A61M 60/531* | (2021.01) |
| *A61M 60/585* | (2021.01) |
| *A61M 60/808* | (2021.01) |
| *A61M 60/81* | (2021.01) |
| *A61M 60/847* | (2021.01) |
| *A61M 60/851* | (2021.01) |
| *A61M 60/857* | (2021.01) |
| *A61M 60/865* | (2021.01) |

(56) References Cited

U.S. PATENT DOCUMENTS

| | | | |
|---|---|---|---|
| 4,818,186 | A | 4/1989 | Pastrone et al. |
| 5,061,256 | A | 10/1991 | Wampler |
| 5,287,858 | A | 2/1994 | Hammerslag et al. |
| 5,507,629 | A | 4/1996 | Jarvik |
| 5,628,731 | A | 5/1997 | Dodge et al. |
| 5,735,892 | A | 4/1998 | Myers et al. |
| 6,007,478 | A | 12/1999 | Siess et al. |
| 6,053,943 | A | 4/2000 | Edwin et al. |
| 6,685,696 | B2 | 2/2004 | Fleischhacker et al. |
| 6,712,844 | B2 | 3/2004 | Pacetti |
| 7,022,100 | B1 | 4/2006 | Aboul Hosn et al. |
| 7,027,875 | B2 | 4/2006 | Siess et al. |
| 7,220,275 | B2 | 5/2007 | Davidson et al. |
| 7,828,710 | B2 | 11/2010 | Shifflette |
| 8,388,565 | B2 | 3/2013 | Shifflette |
| 8,485,961 | B2 | 7/2013 | Campbell et al. |
| 8,535,211 | B2 | 9/2013 | Campbell et al. |
| 8,591,393 | B2 | 11/2013 | Walters et al. |
| 8,597,170 | B2 | 12/2013 | Walters et al. |
| 8,721,517 | B2 | 5/2014 | Zeng et al. |
| 8,734,508 | B2 | 5/2014 | Hastings et al. |
| 8,814,776 | B2 | 8/2014 | Hastie et al. |
| 8,814,933 | B2 | 8/2014 | Siess |
| 8,849,398 | B2 | 9/2014 | Evans |
| 8,932,141 | B2 | 1/2015 | Liebing |
| 8,934,956 | B2 | 1/2015 | Glenn et al. |
| 9,028,216 | B2 | 5/2015 | Schumacher et al. |
| 9,028,392 | B2 | 5/2015 | Shifflette |
| 9,072,825 | B2 | 7/2015 | Pfeffer et al. |
| 9,138,518 | B2 | 9/2015 | Campbell et al. |
| 9,180,235 | B2 | 11/2015 | Forsell |
| 9,446,179 | B2 | 9/2016 | Keenan et al. |
| 9,512,839 | B2 | 12/2016 | Liebing |
| 9,833,550 | B2 | 12/2017 | Siess |
| 9,872,948 | B2 | 1/2018 | Siess |
| 10,052,419 | B2 | 8/2018 | Er |
| 10,208,763 | B2 | 2/2019 | Schumacher et al. |
| 10,357,598 | B2 | 7/2019 | Aboul-Hosn et al. |
| 10,881,770 | B2 | 1/2021 | Tuval et al. |
| 10,894,115 | B2 | 1/2021 | Pfeffer et al. |
| 11,268,521 | B2 | 3/2022 | Toellner |
| 11,280,345 | B2 | 3/2022 | Bredenbreuker et al. |
| 11,724,089 | B2 | 8/2023 | Wallin et al. |
| 11,850,413 | B2 | 12/2023 | Zeng et al. |
| 12,017,056 | B2 | 6/2024 | Guo et al. |
| 2005/0277803 | A1 | 12/2005 | Pecor |
| 2007/0250148 | A1 | 10/2007 | Perry et al. |
| 2009/0012460 | A1 | 1/2009 | Steck et al. |
| 2010/0084326 | A1 | 4/2010 | Takesawa |
| 2013/0267892 | A1 | 10/2013 | Woolford |
| 2014/0148638 | A1 | 5/2014 | LaRose et al. |
| 2015/0238671 | A1 | 8/2015 | Mesallum |
| 2015/0328382 | A1 | 11/2015 | Corbett et al. |
| 2015/0366495 | A1 | 12/2015 | Gable, III et al. |
| 2016/0022890 | A1 | 1/2016 | Schwammenthal et al. |
| 2016/0053763 | A1 | 2/2016 | Toellner |
| 2017/0014562 | A1 | 1/2017 | Liebing |
| 2017/0037860 | A1 | 2/2017 | Toellner |
| 2017/0100527 | A1 | 4/2017 | Schwammenthal et al. |
| 2017/0173242 | A1 | 6/2017 | Anderson et al. |
| 2017/0232169 | A1 | 8/2017 | Muller |
| 2017/0340788 | A1 | 11/2017 | Korakianitis et al. |
| 2018/0080326 | A1 | 3/2018 | Schumacher et al. |
| 2018/0149164 | A1 | 5/2018 | Siess |
| 2018/0256797 | A1 | 9/2018 | Schenck et al. |
| 2018/0303990 | A1 | 10/2018 | Siess et al. |
| 2020/0121835 | A1 | 4/2020 | Farago et al. |
| 2020/0237981 | A1 | 7/2020 | Tuval et al. |
| 2020/0316268 | A1 | 10/2020 | Antoni et al. |

FOREIGN PATENT DOCUMENTS

| | | |
|---|---|---|
| EP | 3153190 A1 | 4/2017 |
| EP | 3000493 B1 | 5/2017 |
| WO | WO01/019444 A1 | 3/2001 |
| WO | WO2015/177793 A2 | 11/2015 |
| WO | WO2018/061002 A1 | 4/2018 |
| WO | WO2018/067410 A1 | 4/2018 |
| WO | WO2018/078615 A1 | 5/2018 |
| WO | WO2018/088939 A1 | 5/2018 |
| WO | WO2018/096531 A1 | 5/2018 |
| WO | WO2019/191851 A1 | 9/2019 |
| WO | WO2019/194956 A1 | 10/2019 |
| WO | WO2020/073047 A1 | 4/2020 |
| WO | WO2021/062265 A1 | 4/2021 |

*130*

*142*

*143*

*140*

*141*

Purge Inlet Port

*137*

*133*

*311*

*139*

*135*

*137*

*132*

*134*

GW & Purge Outlet Port

*136*

Rotary Lip Seal

*138*

Motor

Drive Cable Tube
Junction / Optional
Alignment Bearing
Housing

RO Marker
Band

Proximal Bearing Assembly
(Alignment and Thrust Bearings
on shaft and in Distal Catheter
Cap)

161

162

163

164

165

166

177

178

179

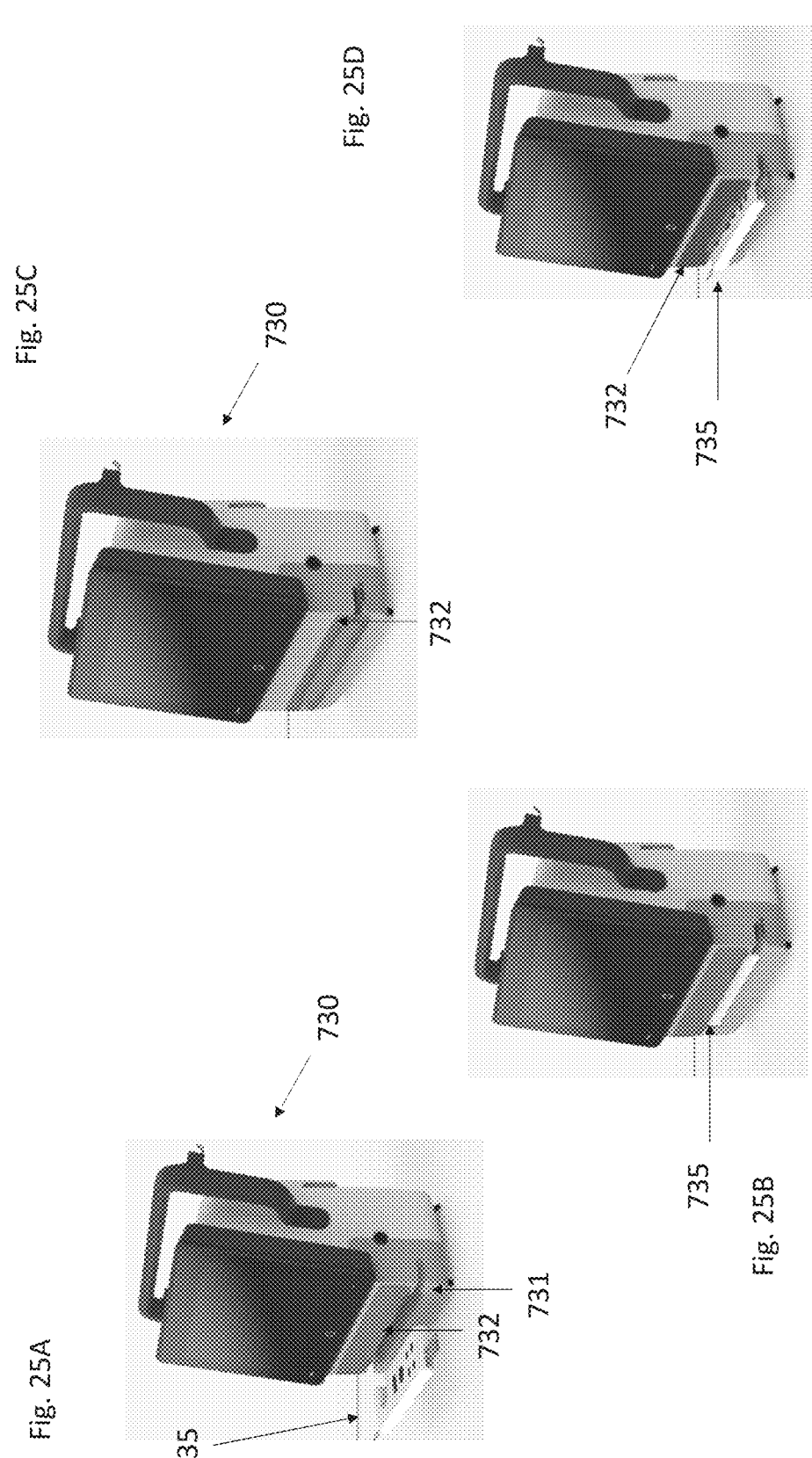

INTRAVASCULAR BLOOD PUMP SYSTEMS AND METHODS OF USE AND CONTROL THEREOF

CROSS REFERENCE TO RELATED APPLICATIONS

This application is a continuation of U.S. application Ser. No. 17/033,482, filed Sep. 25, 2020, which claims the benefit of priority of the following U.S. Provisional Applications, which are incorporated herein by reference in its entirety for all purposes: U.S. Provisional Application No. 62/905,746, filed Sep. 25, 2019, and U.S. Provisional Application No. 62/905,802, filed Sep. 25, 2019.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

One aspect of the device is a removable cassette for use with an external console to facilitate and control the flow of fluid through an intravascular blood pump.

In this aspect, the cassette may include a cassette housing. The cassette housing may include a pump head receiving area sized and configured to receive a pump head therein. The cassette may include a clean fluid pathway between a fluid inlet and a fluid outlet.

In this aspect, a cassette housing may have a first side with a flow control opening formed therein, the flow control opening positioned relative to the clean fluid pathway so as to provide access to the clean fluid pathway from the first side through the flow control opening, the flow control opening sized and configured to receive therein a flow controller of an external console to facilitate the control of fluid through the clean fluid pathway.

In this aspect, the cassette may further comprise a second clean fluid pathway, which may be in communication with a fluid inlet and a second fluid outlet.

In this aspect, a cassette housing first side may further comprise a second flow control opening formed therein, the second flow control opening positioned relative to the second clean fluid pathway so as to provide access to the second clean fluid pathway from the first side through the second flow control opening, the second flow control opening sized and configured to receive therein a second flow controller of an external console to facilitate the control of fluid through the second clean fluid pathway.

In this aspect, the cassette may further include a waste fluid pathway, which may be between a waste fluid inlet and a waste fluid outlet.

In this aspect, a cassette housing first side may further comprise a waste flow control opening formed therein, the waste flow control opening positioned relative to the waste fluid pathway so as to provide access to the waste fluid pathway from the first side through the waste flow control opening, the waste flow control opening sized and configured to receive therein a third flow controller of the external console to facilitate the control of fluid through the waste fluid pathway.

In this aspect, a clean fluid pathway and a second clean fluid pathway may be the same pathway between an inlet and a pathway bifurcation in the cassette.

In this aspect, a bifurcation may comprise at least part of a pressure sensor. In this aspect, a bifurcation may comprise a deformable membrane or diaphragm.

In this aspect, a bifurcation may comprise a pressure sensor housing in fluid communication with a clean fluid pathway.

In this aspect, a fluid outlet and a second fluid outlet may be on a second side of the cassette housing, the second side being orthogonal to an inner side.

In this aspect, a fluid inlet may be on a third side of the cassette housing that is spaced from a second side of the cassette housing.

In this aspect, the cassette may further comprise a waste fluid inlet on a second side of the cassette housing. A waste fluid outlet may also be on the second side of the cassette housing.

In this aspect, any of the flow control openings may extend all the way through an external side of the cassette housing so that a backstop protrusion of a console door can interface with an external side surface of the corresponding fluid pathway to facilitate compressing of the fluid pathway.

In this aspect, a cassette housing may comprise a unitary housing body.

In this aspect, a cassette housing may comprise a body that comprises a plurality of components secured together to form at least part of the housing.

In this aspect, a cassette housing may comprise an internal subassembly that includes a clean fluid pathway, the cassette housing may further comprise one or more shells disposed about the internal assembly.

In this aspect, the cassette may be sized and configured to be secured to an external console to facilitate fluid movement through the fluid pathway when a pump console is activated.

In this aspect, any of the cassettes may be engaged with any suitable external console to facilitate the control of fluid therethrough.

One aspect of the disclosure is an external console (which may be referred to herein as simply console) adapted for use with an intravascular blood pump to control fluid flow therethrough. The external console may include a fluid cassette compartment that is sized and configured to receive therein a removable fluid cassette adapted to be in fluid communication with an intravascular blood pump. The console may include a pump head comprising a plurality of rollers, which may be movable between an inactive state and an active state. A console herein may include a plurality of flow control actuators adapted to be independently controlled and independently moved towards the fluid cassette compartment to facilitate independent control of fluid through a plurality of fluid pathways in a fluid cassette disposed in the fluid cassette compartment.

In this aspect, a plurality of flow control actuators may comprise a plurality of linear actuators that are adapted to be independently moved linearly from the console into the fluid cassette compartment.

In this aspect, flow control actuators may each comprise a stepper motor to cause the linear movement of one of the plurality of linear actuators.

In this aspect, a plurality of flow control actuators may be in communication with one or more computer executable methods (e.g., algorithms) stored in the console that are adapted to independently control each of the plurality of flow control actuators.

In this aspect, a door of the console may be movable between an open state and a closed state, wherein an inner surface of the door includes a plurality of backstops spaced from each other and each protruding from an inner door surface, each of the plurality of backstops aligned with one of the plurality of flow control actuators when the door is in the closed state.

In this aspect, each of the flow control actuators may be adapted to be moved linearly toward one of the plurality of backstops when the corresponding flow control actuator is moved linearly towards the compartment.

In this aspect, the console may include a movable pump head, wherein the pump head comprises a plurality of rollers and is configured to be moved in conjunction with a door lock such that when the dock lock is actuated to look the door in a closed state, the pump head is also moved into an operable state with one of the plurality of fluid pathways in the fluid cassette.

One aspect of the disclosure is a fluid control system for an intravascular blood pump, optionally also methods of use, comprising an external console configured to interface with a fluid cassette to control fluid flow through the cassette and into a blood pump. The system may comprise any of the systems herein in combination with any of the cassettes herein, as well as optionally any of the blood pumps herein. The systems herein may include a console that may include a fluid cassette compartment, a pump head comprising a plurality of rollers, and a plurality of flow control actuators that are each adapted to be independently moved toward the fluid cassette compartment. The systems herein may include a removable fluid cassette. The cassette may be sized and configured to fit within the fluid cassette compartment and to be stabilized therein in at least one direction, the fluid cassette including a plurality of fluid pathways that are each accessible from a first side of the cassette at a plurality of access locations, wherein each one of the plurality of flow control actuators of the console is aligned with one of the plurality of access locations when the fluid cassette is in a closed state to allow each of the flow control actuators to engage one of the plurality of fluid pathways and independently control the flow of fluid therethrough.

In this aspect, a plurality of flow control actuators may each comprise a linear actuator and a stepper motor, the stepper motor adapted to cause linear motion of the corresponding linear actuator toward the fluid cassette compartment and toward one of the fluid pathways.

In this aspect a plurality of fluid pathways may include a catheter fluid pathway, a sheath fluid pathway, and a waste fluid pathway. A plurality of flow control actuators may each be adapted to independently and individually control the flow of fluid through one of the catheter fluid pathway, the sheath fluid pathway, and the waste fluid pathway. In this aspect, the fluid cassette may be in fluid communication with an intravascular blood pump, wherein the catheter fluid pathway is in communication with an clean fluid pathway in a pump catheter, wherein the sheath fluid pathway is in communication with clean fluid pathway in an outer sheath, and wherein the waste fluid pathway is in communication with a waste fluid pathway in the catheter.

One aspect of the disclosure is a fluid control system for an intravascular blood pump, comprising an external console and a fluid cassette, the fluid cassette sized and configured to be positioned in fluid cassette compartment in the external console, wherein the external console and the fluid cassette are together configured with corresponding engagement components to allow the external console to control the flow of fluid through each pathway independently of the other fluid pathways.

BRIEF DESCRIPTION OF THE DRAWINGS

FIGS. 9A-D illustrates an exemplary blood pump that includes a guidewire pathway and at least one clean fluid (e.g., purge) pathway.

FIGS. 25A, 25B, 25C, and 25D illustrate an exemplary external console and an exemplary fluid cassette.

DETAILED DESCRIPTION

The present disclosure is related to medical devices, systems, and methods of use and manufacture. Medical devices herein may include a pump portion adapted and configured to be disposed within a physiologic vessel, wherein the pump includes one or more components that act upon fluid. For example, pump portions herein may include one or more impellers that are configured such that when rotated, they facilitate the movement of a fluid such as blood.

Figure 1:
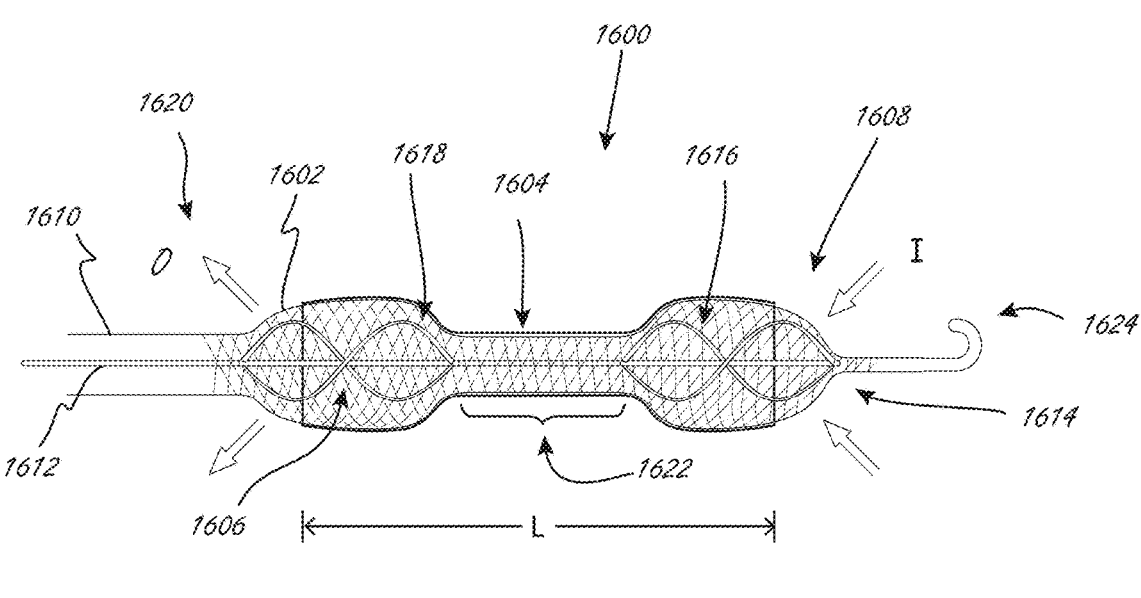
FIG. 1 is a side view of an exemplary pump portion that includes a conduit, a plurality of impellers, an expandable member

FIG. 1 is a side view illustrating a distal portion of an exemplary intravascular fluid pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can in rotational communication with drive cable 1612, directly or indirectly. Drive cable 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Figure 2:
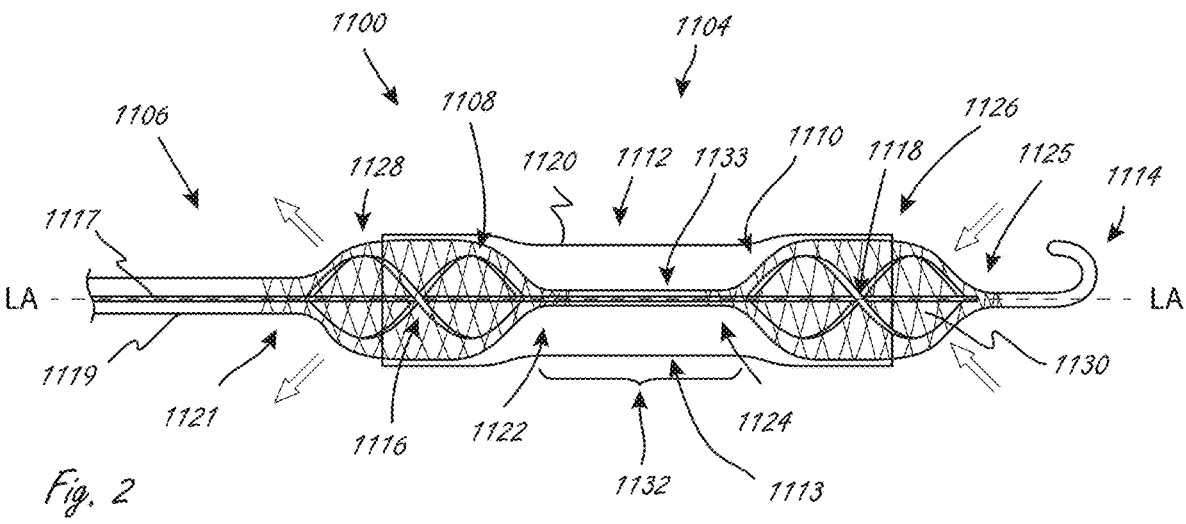
FIG. 2 is a side view of an exemplary pump portion that includes a conduit, a plurality of impellers, and a plurality of expandable members.

FIG. 2 is a side view illustrating a deployed configuration (shown extracorporally) of a distal portion of an exemplary embodiment of a fluid movement system. Exemplary system 1100 includes pump portion 1104 (which as set forth herein may also be referred to herein as a pump portion) and an elongate portion 1106 extending from pump portion 1104. Elongate portion 1106 can extend to a more proximal region of the system, not shown for clarity, and that can include, for example, a motor. Pump portion 1104 includes first expandable member 1108 and second expandable member 1110, axially spaced apart along a longitudinal axis LA of pump portion 1104. Spaced axially in this context refers to the entire first expandable member being axially spaced from the entire second expandable member along a longitudinal axis LA of pump portion 1104. A first end 1122 of first expandable member 1108 is axially spaced from a first end 1124 of second expandable member 1110. Some "expandable members" herein may also be referred to herein as baskets.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Pump portion 1104 also includes blood flow conduit 1112, which in this embodiment is supported by first expandable member 1108 and to second expandable member 1110. Conduit 1112 also extends axially in between first expandable member 1108 and second expandable member 1110 in the deployed configuration. A central region 1113 of conduit 1112 spans an axial distance 1132 where the pump portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a conduit being coupled to an expandable member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations. The conduits herein are considered to create a pathway for fluid to be moved, and may be defined by a one or more components of the pump portion.

Any of the conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as pump portion 1104 is deployed towards the configuration shown in FIG. 2. The conduit may be stretched tightly between the expandable members in some embodiments. The conduit may alternatively be designed with a looseness that causes a greater degree of compliance. This can be desirable when the pump portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the conduits herein, or at least a portion of the conduit, can be impermeable to blood. In FIG. 2, pump portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable members help maintain the conduit in an open configuration by providing radial support for the conduit, while each also creates a working environment for an impeller, described below. Each of the expandable members, when in the deployed configuration, is maintained in a spaced relationship relative to a respective impeller, which allows the impeller to rotate within the expandable member without contacting the expandable member. Pump portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the pump portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and pump portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Pump portion 1104 is adapted and configured to be collapsed to a smaller profile than its deployed configuration (which is shown in FIG. 2). This allows it to be delivered using a lower profile delivery device (smaller French size) than would be required if none of pump portion 1104 was collapsible. Even if not specifically stated herein, any of the expandable members and impellers may be adapted and configured to be collapsible to some extent to a smaller delivery configuration.

The pump portions herein can be collapsed to a collapsed delivery configuration using conventional techniques, such as with an outer sheath that is movable relative to the pump portion (e.g., by axially moving one or both of the sheath and pump portion). For example without limitation, any of the systems, devices, or methods shown in the following references may be used to facilitate the collapse of a pump portion herein: U.S. Pat. No. 7,841,976 or U.S. Pat. No. 8,052,749, the disclosures of which are incorporated by reference herein for all purposes.

FIGS. 3A-3E show an exemplary pump portion that is similar in some ways to the pump portion shown in FIG. 2.

Figures 3A, 3B:
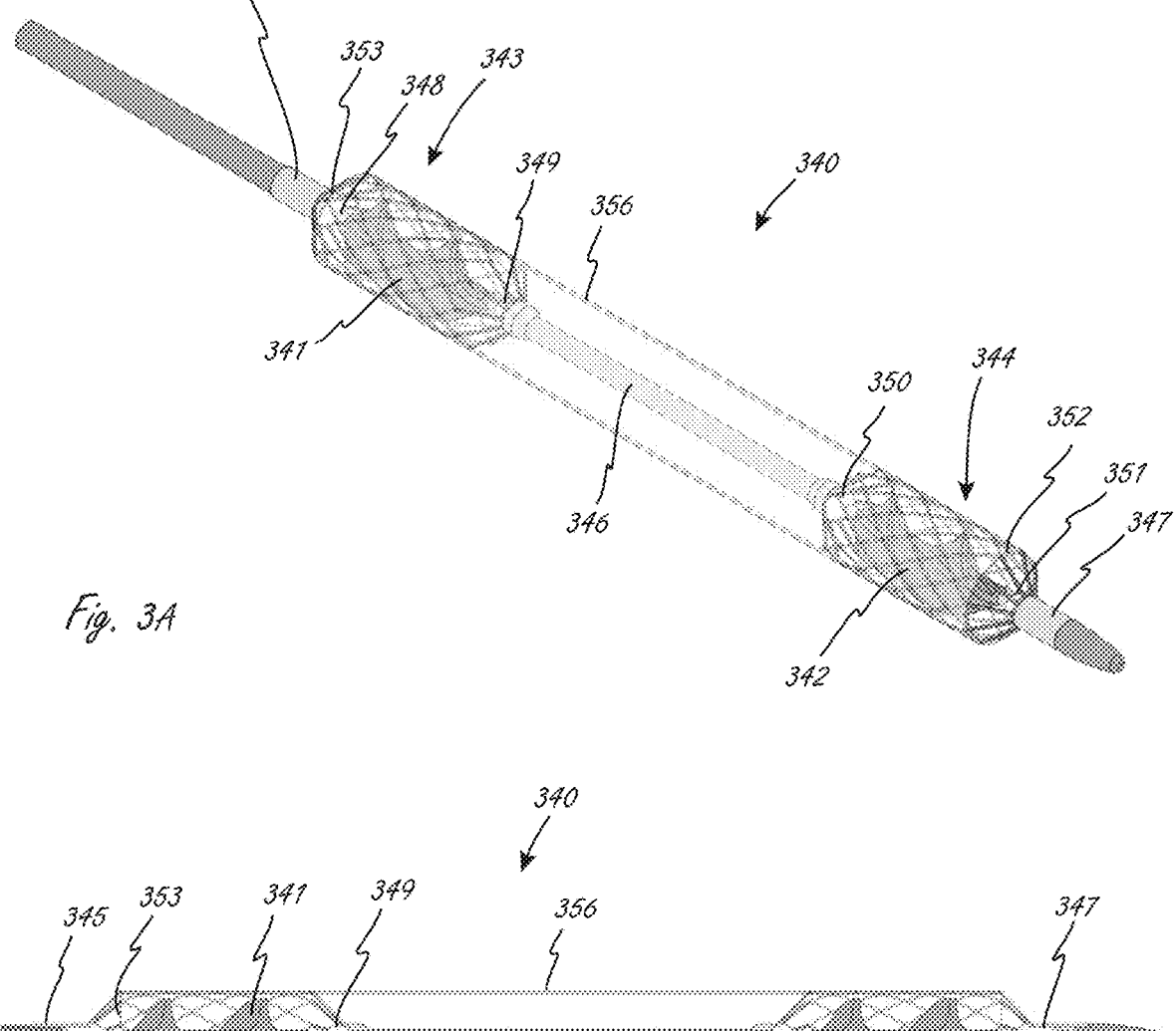
FIGS. 3A, 3B, 3C and 3D illustrate an exemplary pump portion that includes a conduit, a plurality of impellers, and a plurality of expandable members.
Figure 3C:
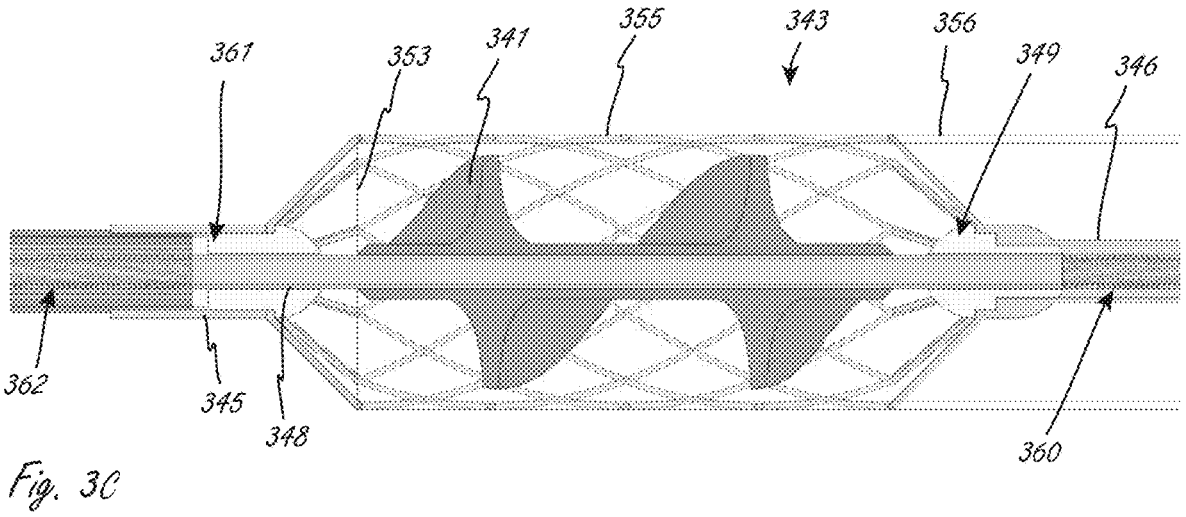
Figure 3D:
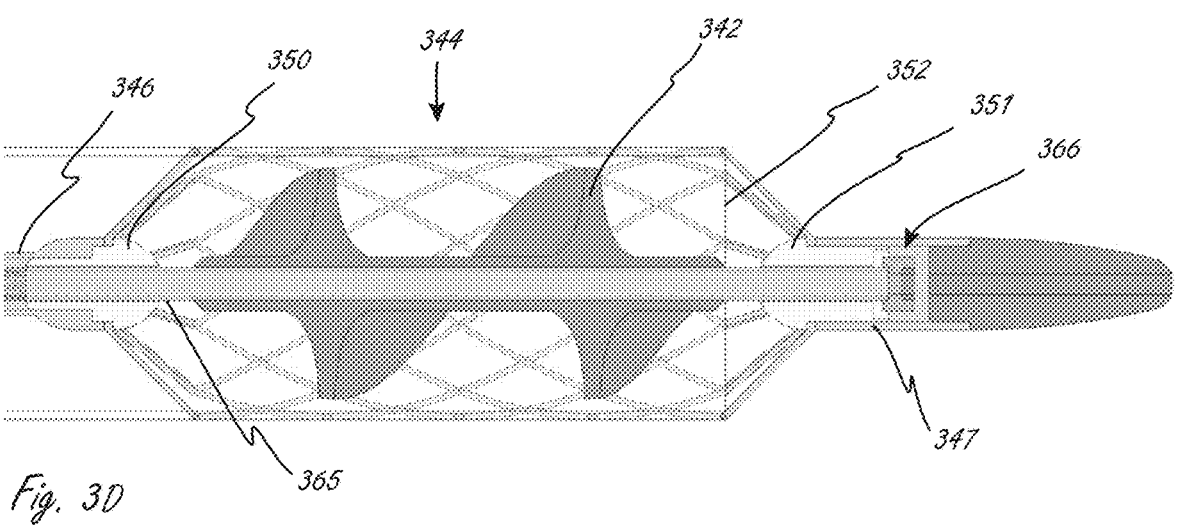

Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the pump portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the pump portion, allowing the pump portion to be, for example, advanced over a guidewire for positioning the pump portion. In this embodiment the second and fourth sections can be stiffer than first and third sections. For example, second and fourth can be tubular and first and third sections can be wound material to impart less stiffness.

Pump portion 340 includes a blood flow conduit, proximal expandable member 343 and distal expandable member 344, each of which extends radially outside of one of the impellers. The expandable members have distal and proximal ends that also extend axially beyond distal and proximal ends of the impellers, which can be seen in FIGS. 3B-3D. That pumps also includes conduit 356, which has a proximal end 353 and a distal end 352. The two expandable members each include a plurality of proximal struts and a plurality of distal struts. The proximal struts in proximal expandable member 343 extend to and are secured to shaft section 345, which is coupled to bearing 361, through which the drive cable extends and is configured and sized to rotate. The distal struts of proximal expandable member 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts of distal expandable member 344 extend to and secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts of distal expandable member extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
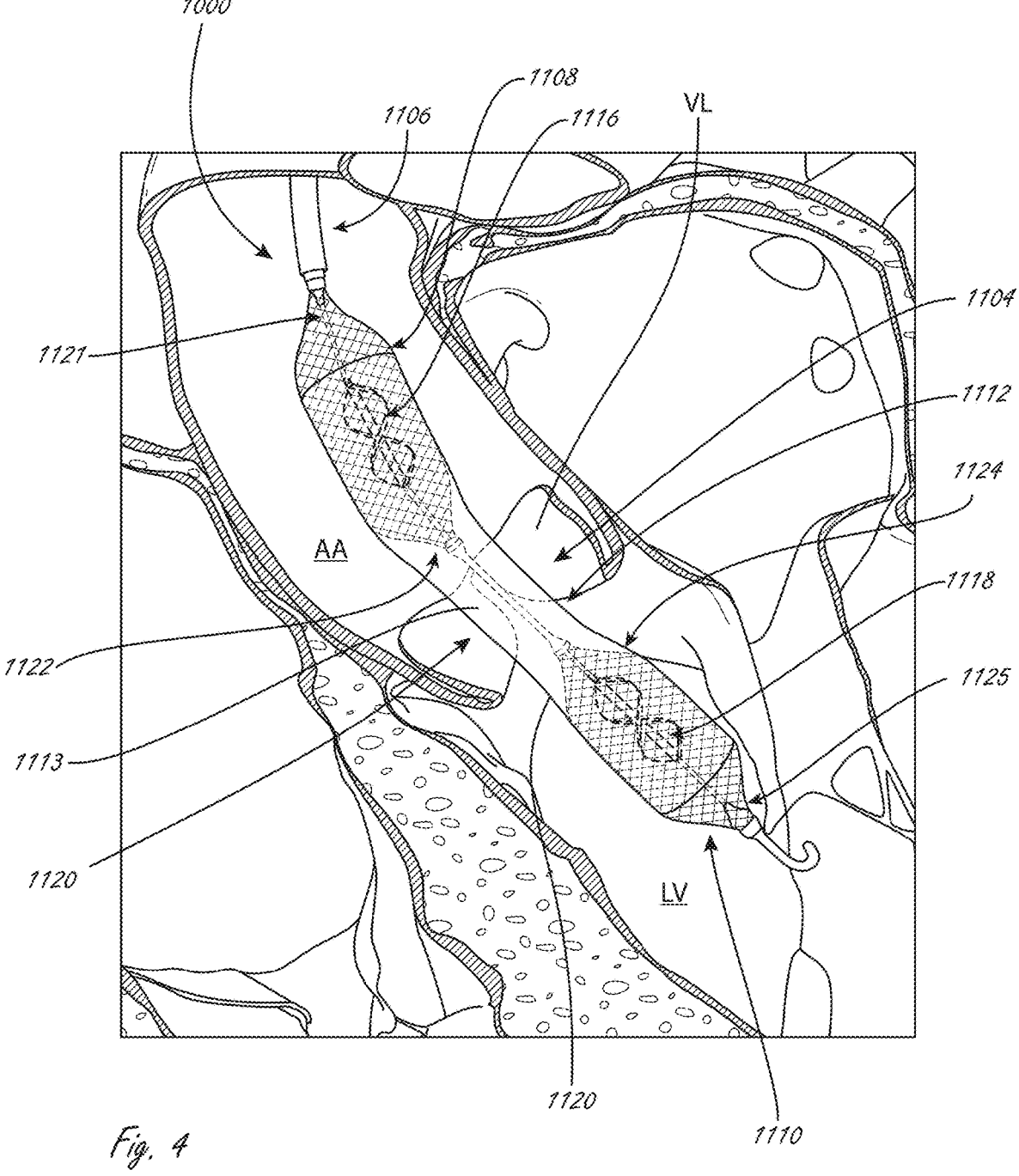
FIG. 4 illustrates an exemplary placement of a pump portion, the pump portion including a conduit, a plurality of expandable members, and a plurality of impellers.

FIG. 4 illustrates an exemplary placement of pump portion 1104 from system 1000 from FIG. 2, and also illustrates an exemplary placement location for any of the pump portions herein. One difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which pump portion 1104 is disposed during delivery to a location near an aortic valve. The sheath or shaft can be moved proximally (towards the ascending aorta "AA" and away from left ventricle "LV") to allow for deployment and expansion of pump portion 1104. For example, the sheath can be withdrawn to allow for expansion of second expandable member 1110, with continued proximal movement allowing first expandable member 1108 to expand.

In this embodiment, second expandable member 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable members 1108 and 1110 causes conduit 1112 to assume a more open configuration, as shown in FIG. 4. Thus, while in this embodiment conduit 1112 does not have the same self-expanding properties as the expandable members, the conduit will assume a deployed, more open configuration when the working end is deployed. At least a portion of central region 1113 of conduit 1112 is positioned at an aortic valve coaptation region. In FIGS. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable member 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable member 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the pump portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the pump at the locations of the impellers, which can allow for more deformation of the pump portion at the location of the leaflets than would occur if an expandable member spanned the aortic valve leaflets. Having a more flexible central region may also cause less damage to the leaflets after the pump portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9F sheath and still obtain high enough flow rates when in use, which is not possible with some products currently in development and/or testing. For example, some products are too large to be able to reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

Embodiments herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 5:
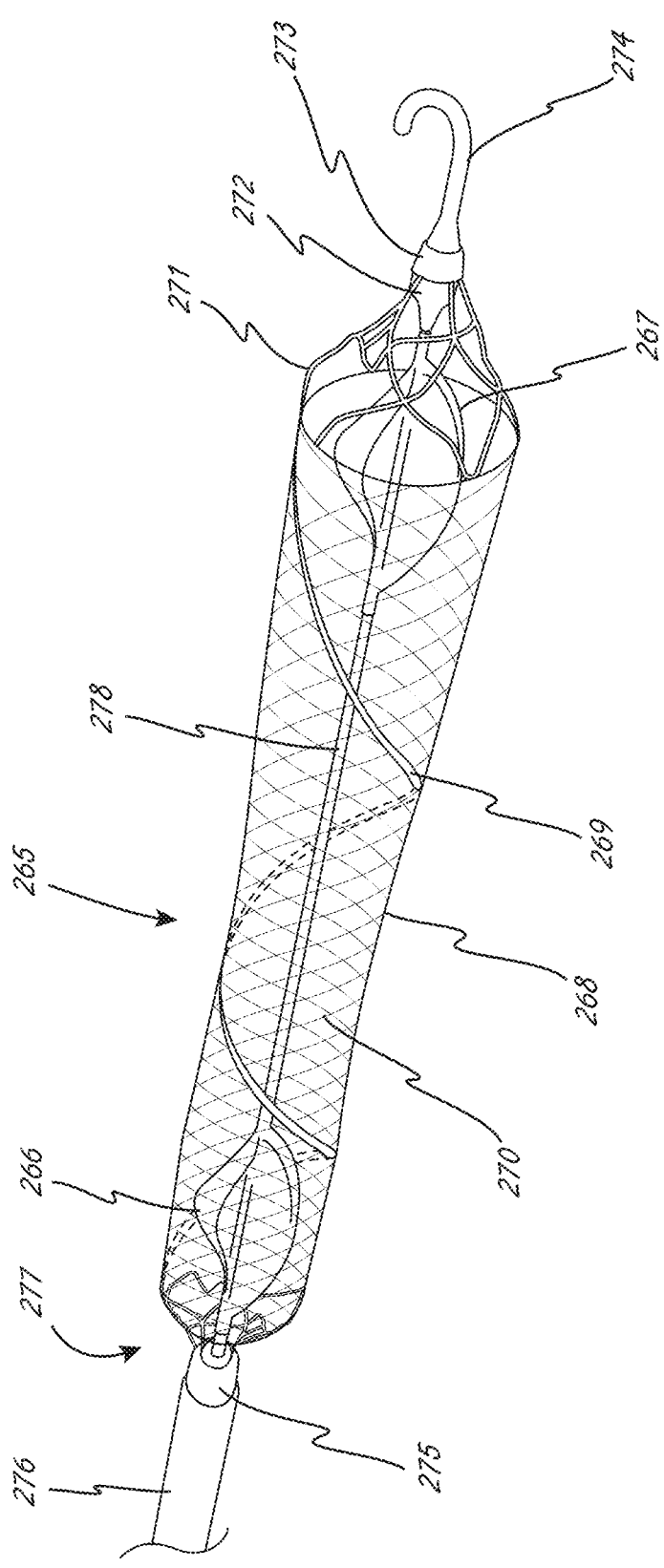
FIG. 5 illustrates an exemplary pump portion.

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable member, referred to 270 generally, and conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member.

There are alternative ways to construct the pump portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the conduits herein act to, are configured to, and are made of material(s) that create a fluid lumen therein between an first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit can extend radially within the expandable member so that inner surface of the conduit is radially within the expandable member where it is secured to the expandable member.

Any of the expandable member(s) herein can be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

In any of the embodiments herein in which the medical device includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

Figures 6, 7:
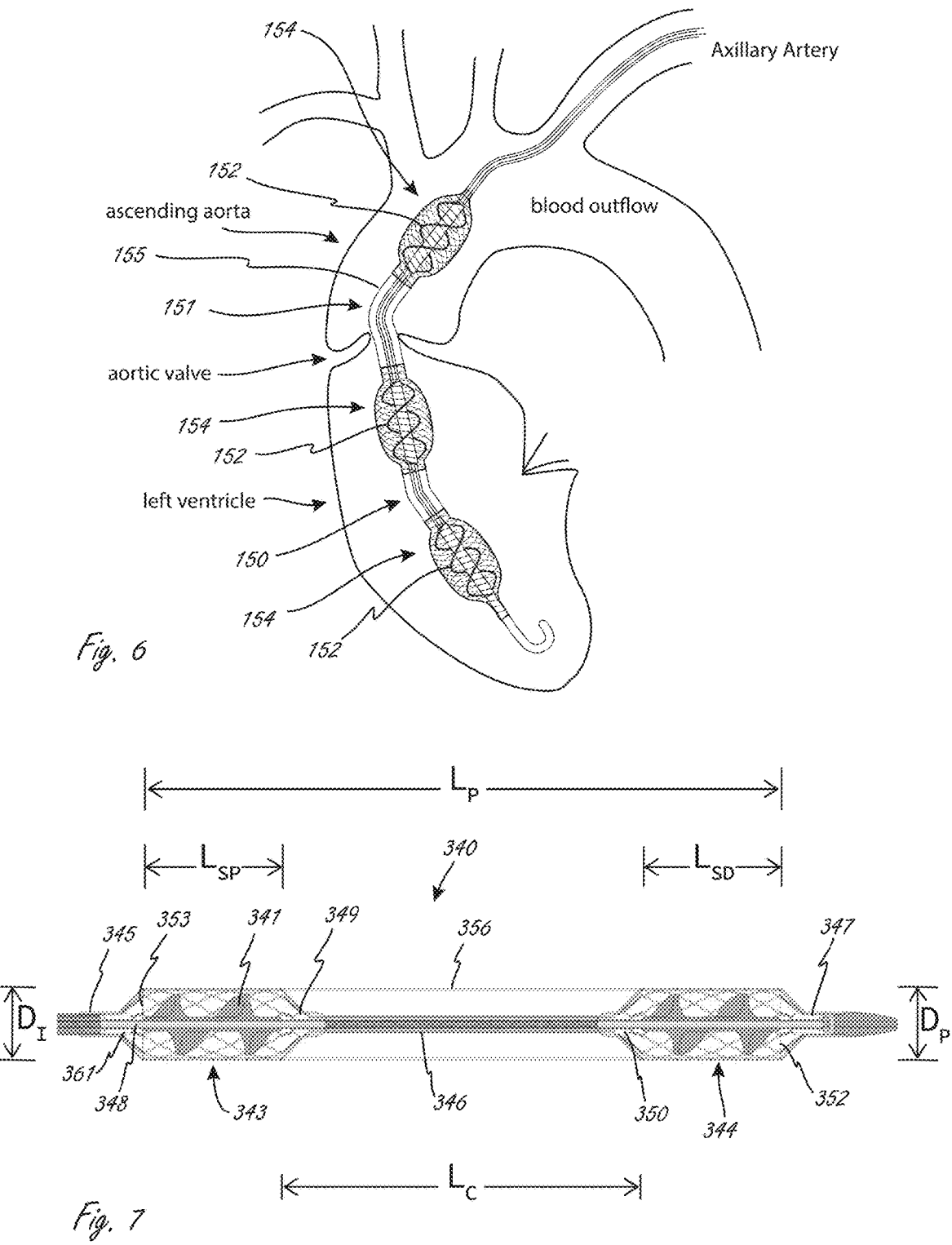
FIG. 6 illustrates a pump portion with multiple impellers, with a bend formed therein between adjacent impellers.
FIG. 7 illustrates a pump portion with a plurality of impellers.

FIG. 6 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 6, a fluid lumen extends from a distal end to a proximal end, features of which are described elsewhere herein. The embodiment in FIG. 8 can include any other suitable feature, including methods of use, described herein.

The embodiment in FIG. 6 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 6. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 6, the pump is positioned via the axillary artery, which is an exemplary method of accessing the aortic valve, and which allows the patient to walk and be active with less interruption. Any of the devices herein can be positioned via the axillary artery. One will appreciate from the description herein, however, that the pump may be introduced and tracked into position in various manner including a femoral approach over the aortic arch.

One aspect of the disclosure is an intravascular blood pump that includes a distal impeller axially spaced from a proximal impeller. In one embodiment, the distal and proximal impellers are separated from each other. For example, the distal and proximal impellers may be connected solely by their individual attachment to a common driveshaft. This is distinct from an impeller having multiple blade rows. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. It can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 7 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 7), from 0.5 cm to 10 cm, or any subrange thereof. The examples below provides exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 7. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 7. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 7. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein, at least one of a flow diffuser or diffusers and a stator or stators is/are located between two or more impellers along the catheter shaft, any one of which can increase fluid pressure between impellers, reduce swirl of the fluid, and/or increase the efficiency of the multiple impellers as a group.

In any of the embodiments herein, features at the fluid exit of an expandable shroud basket or expandable member are shaped to act as a flow diffuser, such as stent-like struts at the attachments between the catheter shaft outer dimension and the expandable member outer dimension, which can be blade-shaped with a twist directed to change the flow direction of blood. In any of the embodiments herein, one or more portions of the catheter shaft downstream of an impeller may flare to a larger diameter to change the angle of blood flow and cause deceleration of the blood flow to a speed closer to native aortic blood flow. Exemplary locations for a larger diameter downstream of an impeller would be at or near the area where an expandable shroud basket attaches to the catheter shaft, and/or at a bearing housing adjacent the impeller, or on or adjacent an internal motor.

In some embodiments, the pump portion can include one or more central members disposed axially in between proximal and distal impellers. The one or more central members may be coupled directly to one another, or they may not. The one or more central members may provide one or more of the following exemplary functions: structural support, flow modification, and maintaining impeller alignment. If the one or more central members provide structural support, the one or more central members may provide structural support to the outer conduit and/or to one or more impellers. For example, they may help maintain tip gap in one or more impellers. In the description that follows, the one or more central members are not in rotational operation with an impeller, unless indicated to the contrary. As used herein, the term "central member" or derivatives thereof does not imply that the member is located at at least a midpoint between two impellers, but simply that the central member is somewhere axially between the two impellers. "Central member" may thus be used interchangeably herein with the term "intermediate member."

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

Any of the pump portions herein that include a plurality of impellers may also include more than two impellers, such as three, four, or five impellers (for example).

While some of the embodiments above describe pump portions or components that are collapsible and expandable (or at least movable between collapsed and expanded configurations), in any of those embodiments the components and expandable outer housing may also be non-expandable and non-collapsible. That is, any of the components in those embodiments may be present, but the components may be non-expandable variations of those components. For example, the impellers above may be non-expandable rather than expandable.

Figure 8A:
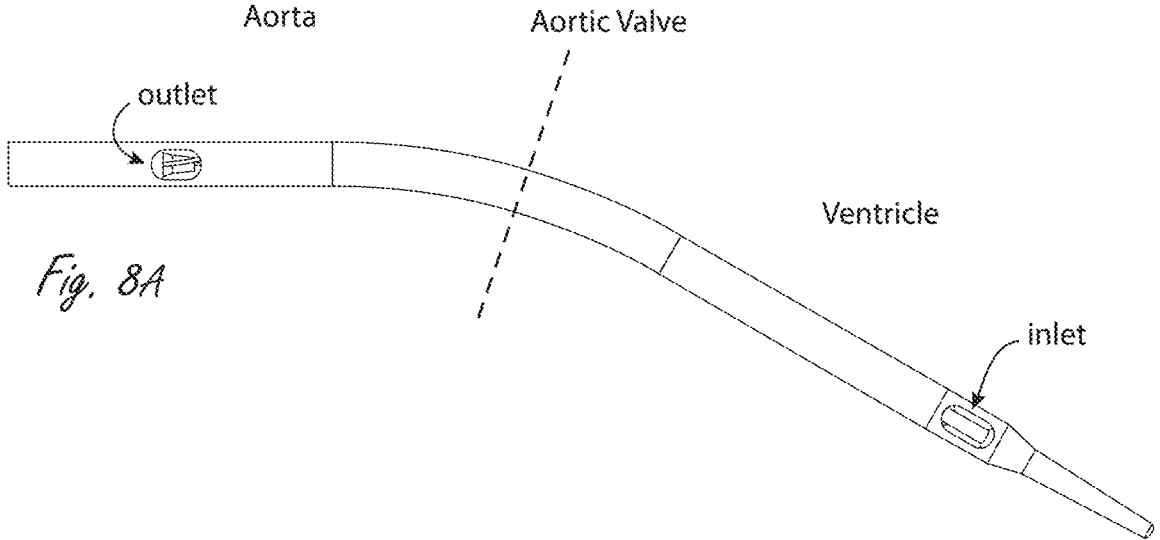
FIGS. 8A and 8B illustrate an exemplary blood pump in which at least the components that are shown are non-collapsible and are not collapsed for delivery.
Figure 8B:
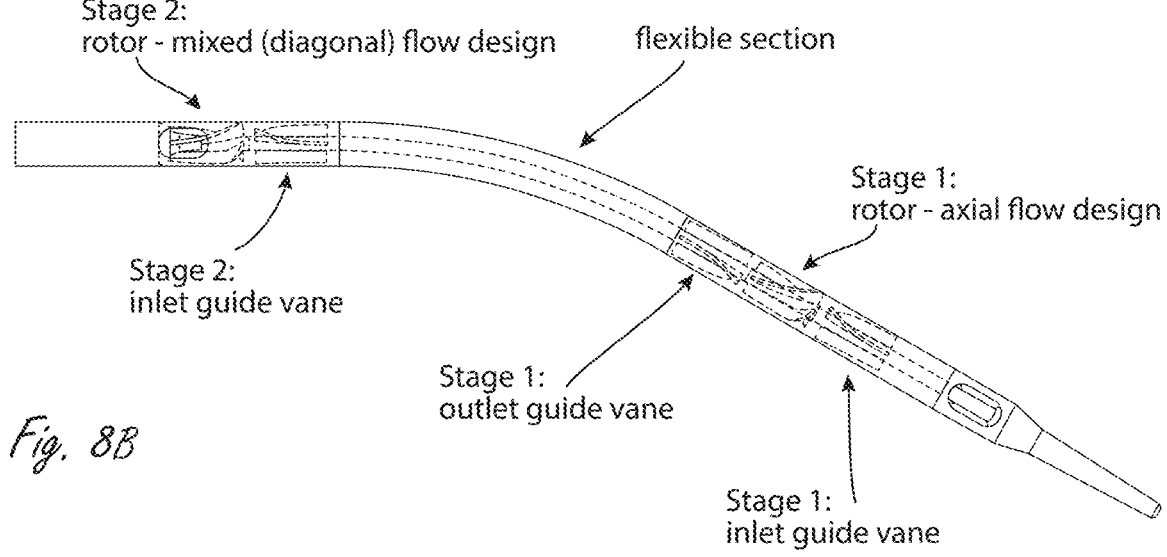

FIGS. 8A and 8B show side views of a distal portion of an exemplary embodiment of a blood pump in which the components are not expandable and collapsible. All the components in this embodiment can be rigid, fixed pieces.

FIG. 8B illustrates internal components that cannot be seen in FIG. 8A. The descriptions in FIGS. 8A and 8B are illustrative and not limiting. The pump portion shown in FIGS. 8A and 8B includes a Stage 1 section and a Stage 2 section, axially spaced apart along the length of the pump portion. In this embodiment the central section between the two stages (labeled generally as "Flexible section") has a bend formed therein, which may extend along any portion of the central section between the stages, such as at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. The bend can be manufactured into the central region so that extracorporally the bend is present, but the central region can be flexible enough so that it can reconfigured to a straightened delivery configuration within a delivery device such as a delivery sheath or introducer.

The pump portion includes a plurality of axially aligned inlet apertures distal to the Stage 1 components. There are two inlet apertures in FIGS. 8A and 8B, but there may be more than two inlet apertures. There are also two outlet apertures that are axially aligned with a portion of the Stage 2 rotor. The inlet and outlet apertures extend through a radially outer wall of the pump portion. Distal is to the right in the figures, and proximal is to the left in the figures. In various embodiments the pump portion includes a set of inlet apertures distal the Stage 1 components and a set of outlet apertures proximal the Stage 2 components. In various embodiments the pump portion includes a set of inlet apertures distal the distal pump and a set of outlet apertures proximal the proximal pump. In various embodiments, no apertures (for inlet or outlet) are between the Stage 1 and Stage 2 components. In various embodiments, no apertures (for inlet or outlet) are between the distal and proximal pump impellers.

Stage 1 in this embodiment includes a distal impeller (labeled as Rotor), an inlet guide vane distal to the rotor, and an outlet guide vane proximal to the distal rotor. The vanes (and any vanes herein) are considered generally to be flow modification elements or a derivative as that term is used herein. Any of the vanes and rotors can include a hub and extending blades as shown, or can include other known impeller and stator/vane designs. The vanes (and any flow modification components herein) are positioned closely next to the distal impeller, such as less than 10 mm away (along the length of the device), or less than 9 mm away, or less than 8 mm away, or less than 7 mm away, or less than 6 mm away, or less than 5 mm away, or less than 4 mm away, or less than 3 mm away, or less than 2 mm away, or less than 1 mm away. "Closely" as used herein can include any of these axial distances. "Closely" as used herein can also refer to a distance less than two times a diameter of the central lumen.

Stage 2 in this embodiment includes a proximal impeller (rotor) and an inlet guide vane distal to the proximal impeller. All of the disclosure above related to the vanes in Stage 1 is incorporated and can be incorporated into Stage 2 vanes.

In this example, the Stage 1 (distal) rotor is configured as an axial flow impeller, and proximal impeller (Stage 2) is configured as a mixed (diagonal) flow impeller, but these are illustrative and other impeller designs can be used for either impeller.

The pump portion in this embodiment includes a flexible outer housing between the stages. The flexible outer housing can be, for example, a flexible polymeric material that is formed with a slightly degree of curvature and can be straightened for delivery, and is coupled to the distal stage and proximal stage sections. In some embodiments the flexible central section could be a very thin walled rigid material, which imparts some flexibility. In other embodiments, for example, the flexible section could include a plurality of elongate support members (e.g., nitinol wires) to which a flexible membrane is attached. The elongate support members can be formed with bends therein and spaced around the periphery of the flexible section, so that the flexible membrane forms a lumen therethrough. In some embodiments, the flexible section can include a laser cut tube (e.g., laser cut polymeric or metallic material, e.g., nitinol) with one or more slots cut out in at least a section to impart flexibility (e.g., creating a spine along one side with ribs extending around at least a portion of the periphery, the ribs formed by cutting out material), and a membrane like material can be affixed to the slotted tubular member to cover the removed material. The flexible material could also include a stent like device that is configured with a bend, and a membrane like material covering the stent apertures.

As used herein, "axially spaced" includes embodiments in which a bend exists in the outer profile (e.g., FIGS. 8A and 8B), wherein a bend can be included in any of the embodiments herein. Axially spaced as that phrase is used anywhere herein is meant to refer to spacing along the device, even if there is a bend in the outer profile of the pump portion (e.g., FIGS. 8A and 8B). It may refer to spacing along a longitudinal axis of the pump portion, for example.

In alternative embodiments to that shown in FIGS. 8A and 8B, not all components shown need to be included. For example, any of the vanes may not be present, depending on flow needs.

Any of the other disclosure herein related to any aspect of a pump device or method of use (e.g., external motors, placement when used) is incorporated by reference into the embodiments in FIGS. 8A and 8B.

The description shown in FIG. 8A illustrates an exemplary placement of the device, showing surrounding/ambient anatomy. The distal impeller can be positioned in the left ventricle while the proximal impeller is positioned in the ascending aorta, and the impellers can be spaced accordingly.

Blood pumps, such as any of the intravascular pumps herein, may benefit from having one or more fluid paths through which fluid can flow through the device. For example without limitation, blood pumps may benefit from having one or more fluid paths through which fluid can flow to perform one or more exemplary functions, such as: cooling rotating components (e.g., a drive cable) to prevent their overheating; flushing small particulates that may break off rotating components (e.g., a drive cable) to prevent the rotating parts from being damaged by the small particulates; lubricating rotating components (e.g., one or more bearings), and preventing blood ingress into the pump (e.g., near or at a distal end of the pump). Fluid delivery through the one or more flow paths may provide any number of these functions.

Figure 9A:
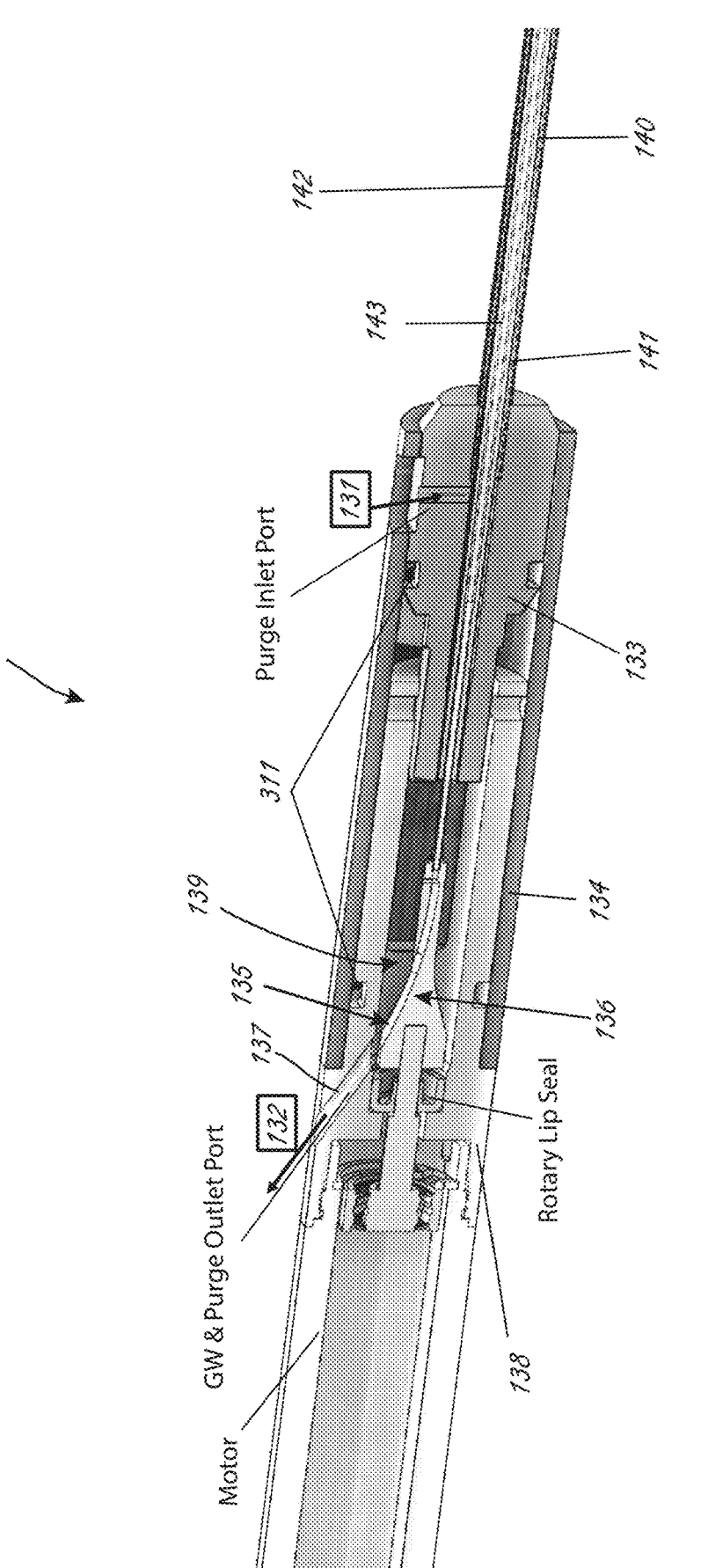

FIGS. 9A-9D illustrate an exemplary embodiment of a fluid delivery system incorporated into an exemplary fluid pump (e.g., blood pump) with a fluid inlet port and a fluid outlet port. FIG. 9A illustrates a portion of the device that is proximal to the one or more impellers, and in this embodiment includes a proximal end of a catheter, a motor assembly that causes the rotation of a drive cable and impeller(s), a fluid inlet port, and fluid outlet port, and a guidewire port that allows access to a guidewire pathway or lumen.

Figure 9B:
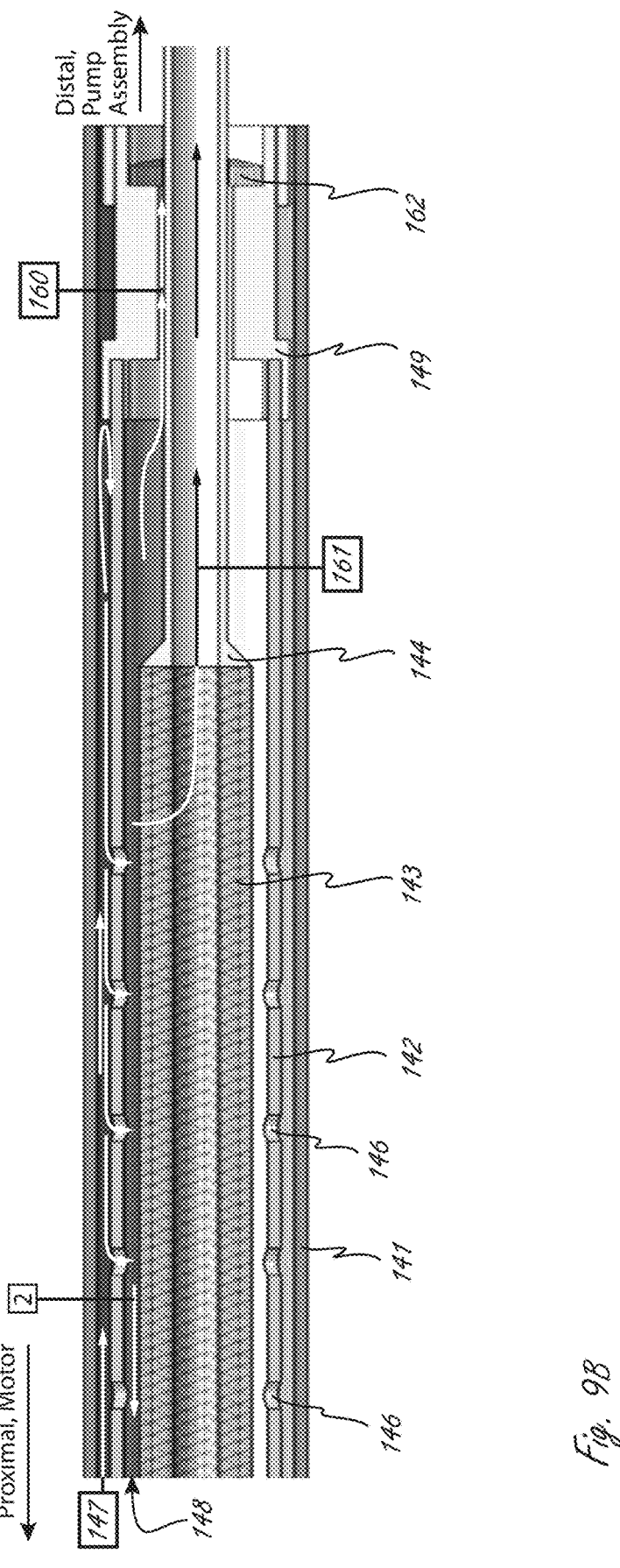
Figure 9C:
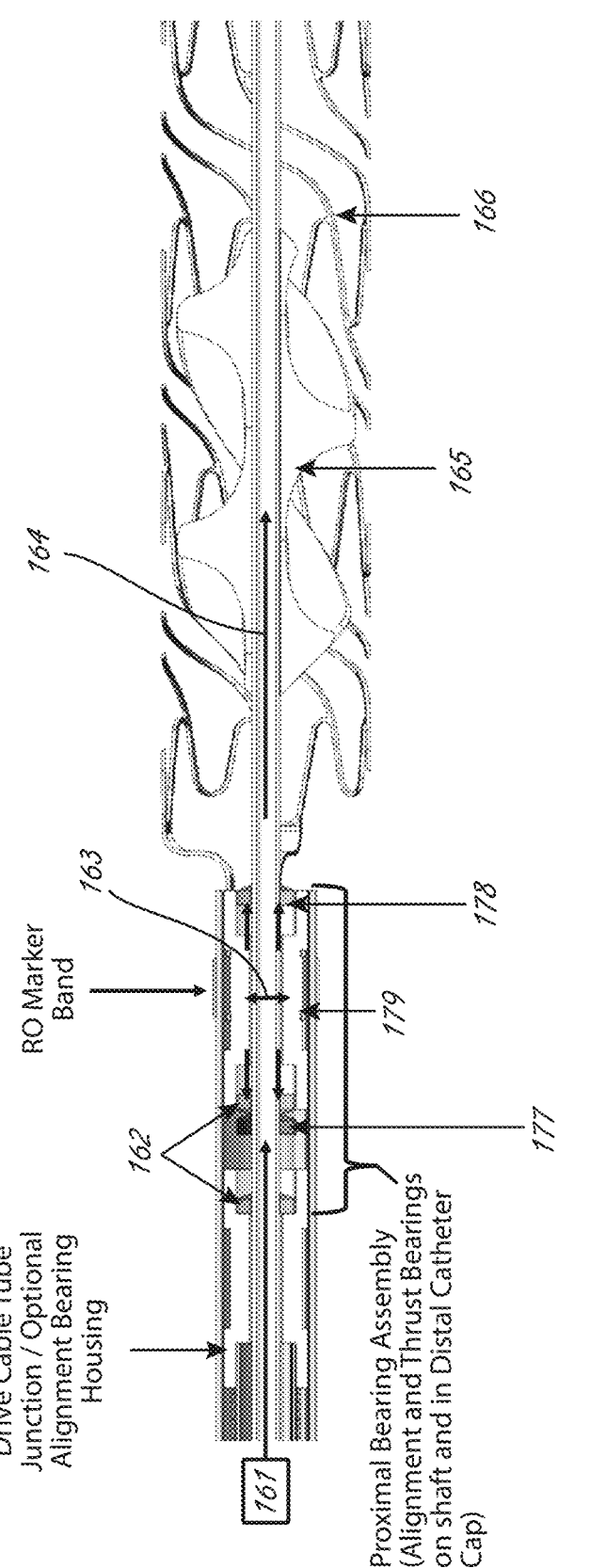
Figure 90:
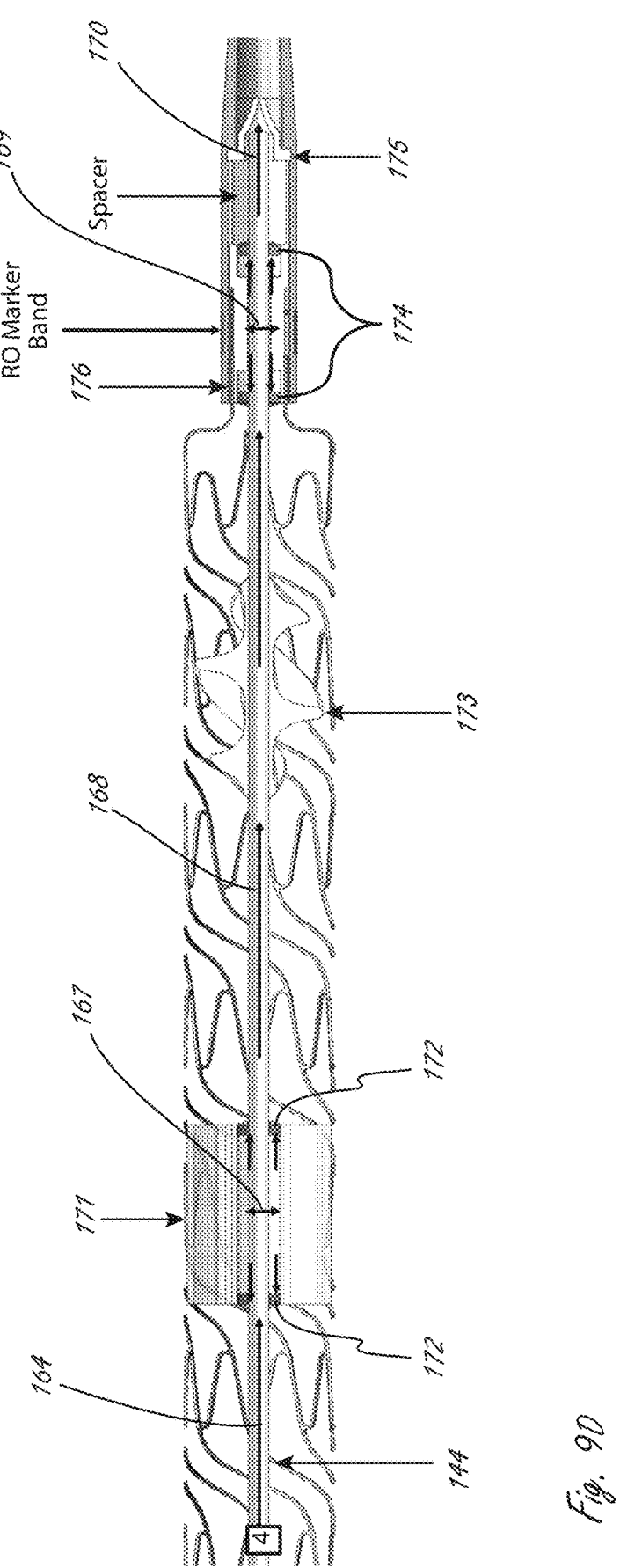

FIG. 9B shows a region of an exemplary blood pump that is distal to the region shown in FIG. 9A, but includes some of the catheter components that are shown in FIG. 9A. FIG. 9C shows a region of the blood pump distal to the region in FIG. 9B, and FIG. 9D shows a region of the blood pump distal to the view in FIG. 9C.

While FIGS. 9A-9D illustrate different sections of an exemplary blood pumping device, it is understood that in alternative embodiments aspects of the system can vary. For example, in alternative embodiments the portion of the device with the impellers can vary and could only include a single impeller, or the expandable housing around the impeller could have a wide variety of configurations. It is understood that individual regions of the device can be incorporated by themselves into a variety of different types of blood pumps.

One aspect of this exemplary embodiment includes a guidewire access port that also functions as a fluid port, and in this embodiment a fluid outlet port. A motor sealing cap 138 includes, formed therein, a guidewire channel 137, including a guidewire port in a radially side surface that provides access from outside the device to channel 137. The motor sealing cap may be an optional component, and the guidewire channel 137 can alternatively be formed in a different part of the device (e.g., which may not function as a motor sealing cap). The device also includes drive cable coupler 135, which includes formed therein a guidewire channel 136, which is a portion of a guidewire pathway. Drive cable coupler 135 is rotated by the motor, and causes the rotation of drive cable 143, which causes rotation of the one or more impellers in the pump portion. These components are thus considered to be in rotational communication. Channel 137, including the guidewire port, is formed in the device and is not adapted to rotate when the motor rotates. Channel 136 formed in drive cable coupler 135 rotates when the drive cable coupler rotates. When drive cable coupler 135 is in the position shown in FIG. 9A, channel 137 is in alignment with channel 136, which allows a guidewire to be advanced through or removed from channel 137 and through channel 136. If the guidewire is being inserted, the guidewire can then be advanced further distally through the entire device and out a distal end, described in more detail below. As is also described in more detail below, the guidewire access port also acts as a fluid outlet port that allows return fluid to flow from return area 139 out of the outlet port.

One of the advantages of having the guidewire access port (part of channel 137) in the location that it is in this embodiment, is that, if needed after the pump portion has already been advanced to a location within the patient, a guidewire can be reinserted into the port and inserted all the way to and out of the distal end. Importantly, the guidewire can be reinserted without having to remove most of the device from the patient like with some rapid exchange designs, and without having to remove the motor assembly. This exemplary embodiment thus allows easy reentry of a guidewire without having to remove the motor assembly, and without having to remove the device from the subject.

Being able to reinsert the guidewire during use can be advantageous because it can, for example without limitation, allow for repositioning of the pump portion if desired or needed. For example, if the pump portion moves out of position relative to an anatomical landmark (e.g., an aortic valve), a guidewire may need to be inserted to safely reposition it relative to the anatomical landmark.

Because the guidewire path extends through a rotational component (e.g., drive cable coupler 135), it is important that the guidewire not be present in the guidewire path when the rotating component is active. The apparatuses herein can also include an automated sensing mechanism to detect the presence of the guidewire in the guidewire pathway, and/or a prevention mechanism that prevents the motor from being activated if the guidewire is in the lumen. For example without limitation, there could be a sensor that can selectively detect the presence of the guidewire in the guidewire pathway, and communicate that to a controller that prevents the motor from being activated.

In this embodiment there is a single fluid inlet channel or lumen 131 into which fluid can be delivered into the device. FIG. 9B illustrates a region of the device and illustrates different pathways the fluid can take after it has been delivered into the device. After the fluid is advanced into fluid inlet port channel 131 (which includes an inlet port), it travels through a space 147 between clean purge tube 141 and drive cable tube 142. This is considered clean input fluid. This pathway dead-ends at distal catheter cap 149. The fluid passes through the one or more apertures 146 formed in a distal region of drive cable tube 142 as shown in FIG. 9B, entering into an annular space between drive cable tube 142 and drive cable 143. Some of this fluid (optionally most of the fluid) returns in the proximal direction through this annular space, lubricating and cooling drive cable 143 and flushing potential particulate along its path. This return fluid continues to flow proximally and into area 139 shown in FIG. 9A, and continues to flow through channel 137 and out of the fluid port (which is also the guidewire access port). A fluid outlet port thus also functions as a guidewire access port in this embodiment.

While most of the fluid returns proximally to area 139, some of the fluid, after it passes through apertures 146, continues distally beyond the distal end of the drive cable 143. Some of the fluid follows proximal bearing path 160 through alignment bearing 162 to prevent blood ingress. Fluid flow along path 160 to bearing 162 can be controlled by, for example, controlling input flow pressure and throttling of the return fluid at the proximal region of the device.

Some of the fluid, after passing through apertures 146, will flow through drive cable 143, along path 161, and will continue distally through the device (e.g., through hypotube 144) and out holes to lubricate any rotating surfaces and to prevent blood ingress, described in more detail below. Guidewire lumen 145 is thus positioned to also function as a distal bearing fluid flow path.

Some fluid flows distally along path 161, as shown in FIG. 9C, and passes through holes along path 163, to lubricate one or more of bearings 162, thrust bearing 177, and alignment bearing 178. Some of the fluid continues distally in the direction of arrow 164 shown in FIG. 9C, through impeller 165 (which in this embodiment is a proximal impeller). Some of the fluid passes through apertures along path 167 to lubricate optional alignment bearings 172 that support central member 171, which may be any of the collapsible support members, including any of the central or intermediate members herein. Some fluid continues distally through the guidewire lumen in the direction of arrow 168, through optional distal impeller 173. Some fluid passes through holes along path 169 to lubricate bearings 174 that are distal to the distal impeller. Some of the fluid may also flow through valve 175 and out the distal end of the device, helping prevent blood ingress.

In this exemplary embodiment a single flow path flowing through a tubular member (path 161 that extends distally through guidewire lumen shown in FIG. 9B) leads to (is in fluid communication with) at least three distally located bearing lubricating fluid paths, 163, 167, and 169, which lubricated three axially spaced bearing regions. In some alternative embodiments, there may be a single bearing region that is lubricated, two bearing regions that are lubricated, or even more than three bearings regions that are lubricated, depending on the number of structures disposed within the expandable housing that require bearings and thus lubrication.

An exemplary method of using the device in FIGS. 9A-D includes inserting a guidewire near a target location (e.g., into a left ventricle via femoral artery access), then feeding the distal guidewire port over the guidewire and advancing the device over the guidewire towards the target location (e.g., an aortic valve). The method can also include removing the guidewire from the guidewire path, and coupling the proximal portion shown in FIG. 9A to a fluid inlet coupler and a fluid outlet coupler at the inlet and the outlet fluid locations, respectively. The motor can be activated to activate the one or more impellers. If the guidewire needed to be reinserted, the fluid out connector can be removed and a guidewire can be reinserted (e.g., for repositioning). The guidewire can then be removed and the fluid outlet coupler can again be put into fluid communication with the guidewire pathway. These methods or any of them individually can be incorporated into the use of any of the suitable devices herein, such as the device in FIGS. 10A and 10B. Additionally, any of the steps in any of the other exemplary methods of use herein, such as those below, may be incorporated into a use of the blood pump in this embodiment.

Figure 10A:
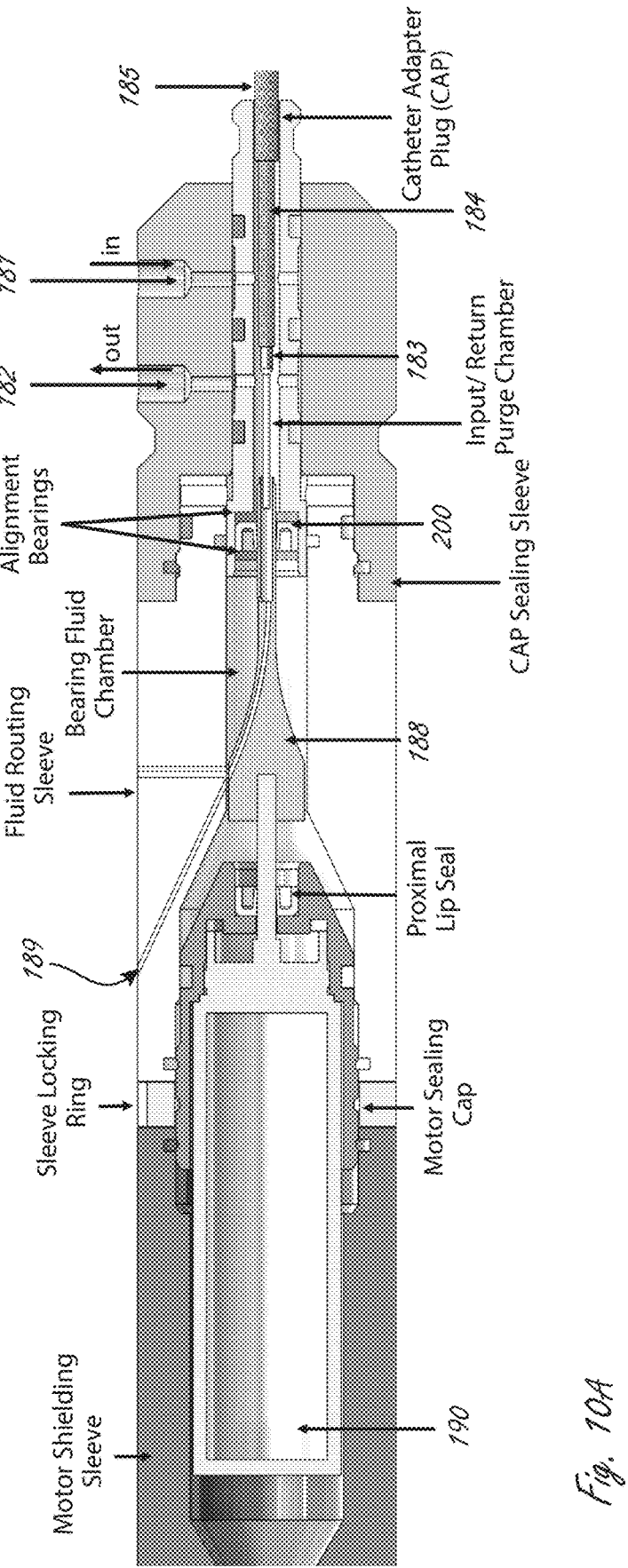
FIGS. 10A and 10B illustrates an exemplary blood pump that includes a guidewire pathway and at least two clean fluid pathways (e.g., purge) that are not in fluid communication.
Figure 10B:
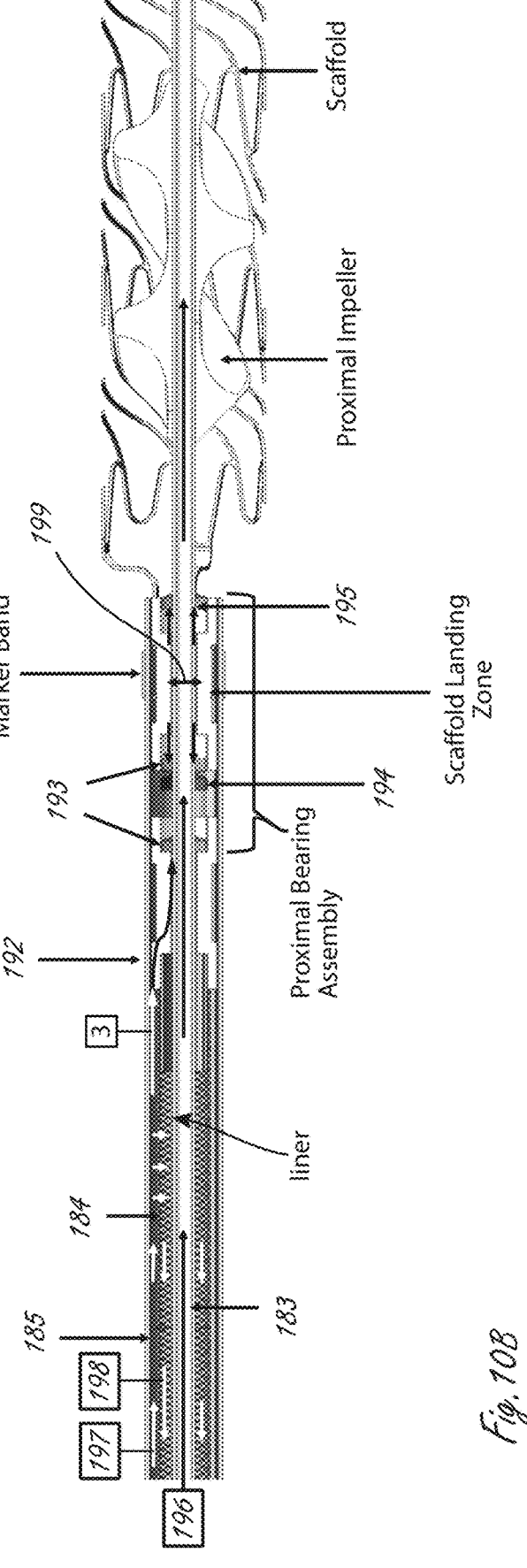

FIGS. 10A and 10B illustrate an exemplary embodiment of a fluid delivery system incorporated into an exemplary fluid pump (e.g., blood pump) with a first flow path with a first fluid inlet port and a first fluid outlet port. In this embodiment, however, there is also a second fluid flow path that is not in fluid communication with the first flow path. The device 180 in FIGS. 10A and 10B is similar to that shown in the embodiment in FIGS. 9A-D, except in this embodiment the fluid path 161 from FIG. 9B does not originate as fluid that flows through the drive cable. In this embodiment the fluid flow path that includes the guidewire lumen (see fluid path 196 in FIG. 10B) is in fluid communication with a separate and second fluid inlet port 189, which is also located to function as a guidewire access port, as shown in FIG. 10A. Drive cable 183 has a drive cable liner 187 on its inner surface to seal off the distal bearing flow path 196 (through the guidewire lumen). In this embodiment the guidewire access port does not function as a fluid outlet, like in FIGS. 9A-D, but as a fluid inlet port, and thus still functions as a fluid port or fluid access.

The blood pump also includes a first fluid path that includes inlet port 181 and outlet port 182 as shown in FIG. 10A. This flow path is very similar to the path in FIGS. 9A-D, except that it does not include the path through the drive cable and hypotube (i.e., does not include the guidewire lumen). The fluid is advanced through port inlet port 181, flows distally along path 197 in FIG. 10B, which is between clean purge tube 185 and drive cable tube 184. This path dead-ends at a distal catheter cap, just as in the embodiment in FIGS. 9A-D. The fluid flows through holes in drive cable tube 184, and returns proximally in the annular space between drive cable tube 184 and drive cable 183. In this part of the path the fluid lubricates and cools the drive cable and flushes potential particulate along its path, carrying them proximally to fluid exit port 182 shown in FIG. 10A. Seal 200 prevents fluid from passing proximally to seal.

Fluid flowing through the first fluid path thus lubricates and cools the drive cable, as well as flushes potential particulates and returns to exit port 182. Fluid flowing through the second fluid path travels further distally through the system, and lubricates one or more distal bearings, just as in the embodiment in FIGS. 9A-D. For example, path 199 shown in FIG. 10B is the same as path 163 in FIG. 9C, which lubricates bearings in that bearing region. While not shown, the fluid flow path distal to the view shown in FIG. 10B can be exactly the same as in FIG. 9D, thus lubricating additional bearings, and optionally exiting through a valve at a distal end of the device. This second flow path can thus also prevent ingress of blood, which is described more fully in FIGS. 9A-D.

In any of the devices herein, the pump portion can include a distal end valve distal to the impeller to seal off the distal guidewire port after the guidewire is removed, but allows for guidewire reinserting therethrough.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different.

Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 11A:
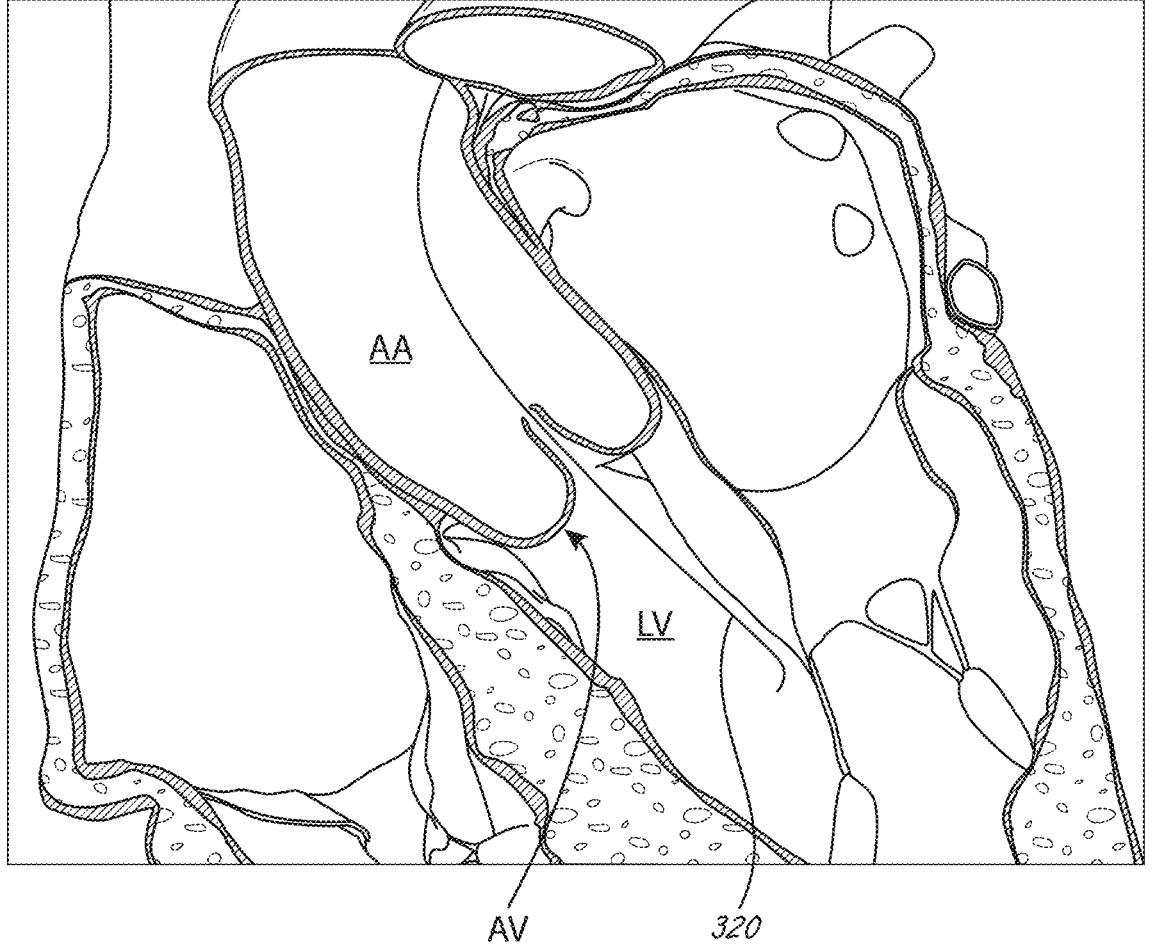
FIGS. 11A-11F illustrate an exemplary sequence of steps that may be carried out based on an exemplary method of using an exemplary blood pump.
Figure 11B:
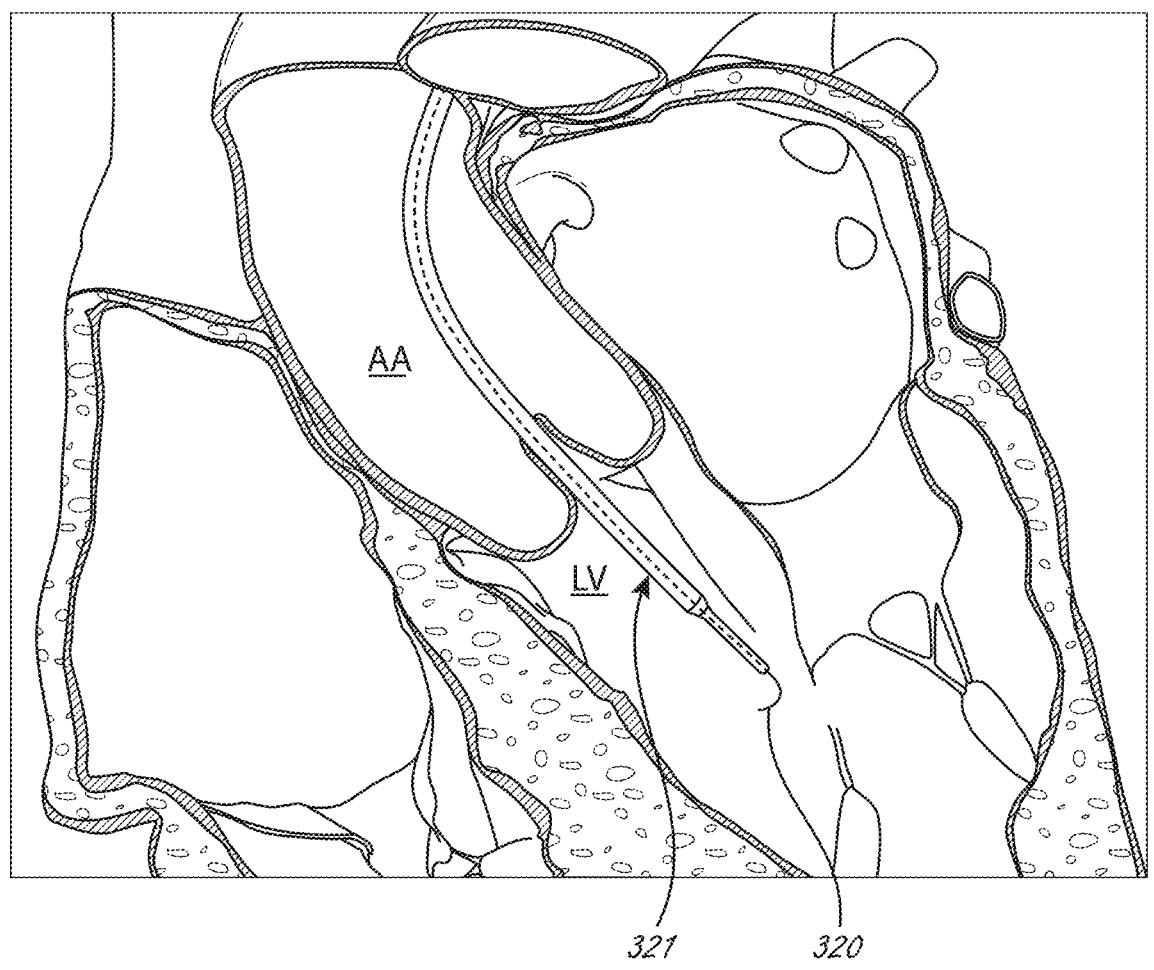

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 11A), and the blood pump 321 (including a catheter, catheter sheath, and pump portion within the sheath; see FIG. 11B) can be advanced over the second wire towards a target location, such as spanning an aortic valve "AV," and into a target location (e.g., left ventricle "LV"), using, for example, one or more radiopaque markers to position the blood pump.

Figure 11C:
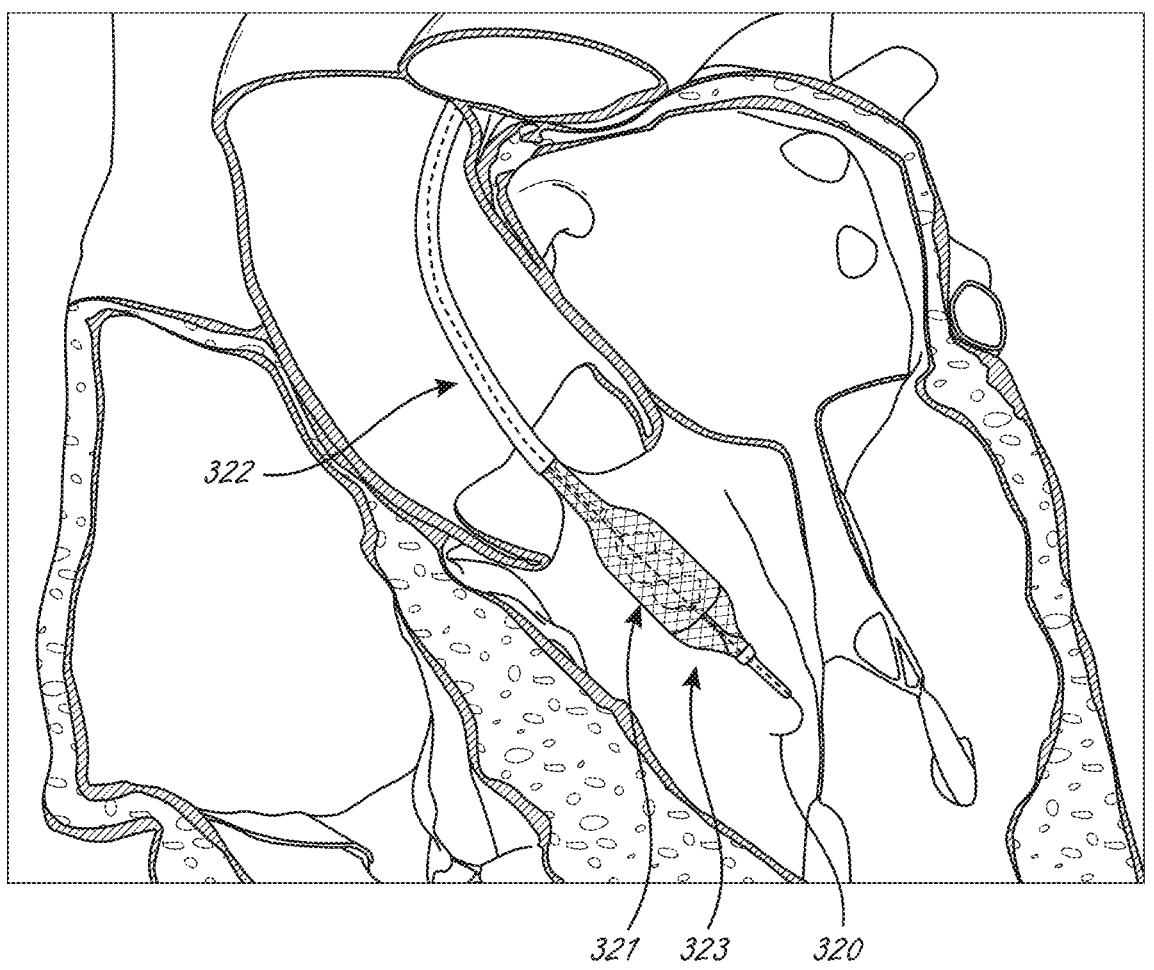
Figure 11D:
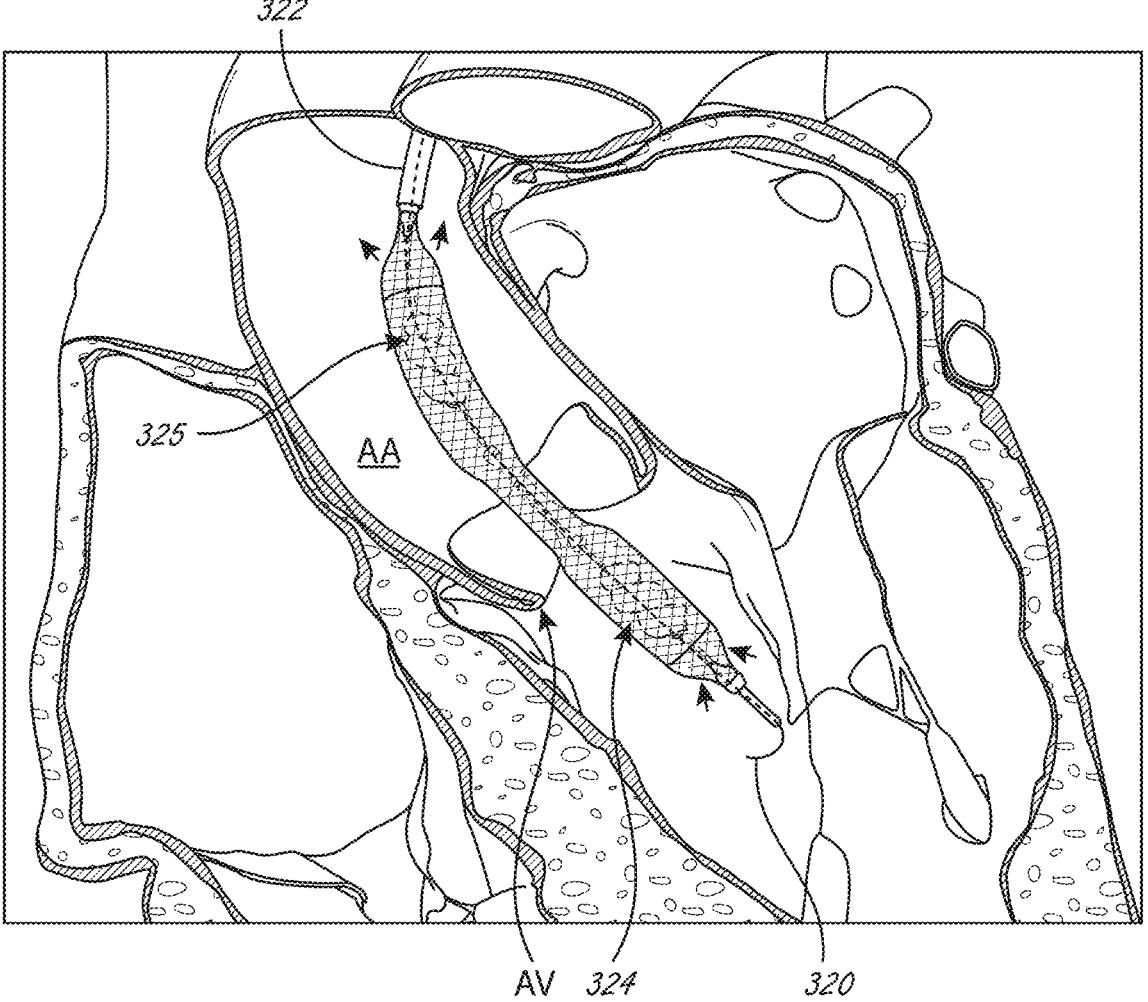

Once proper placement is confirmed, the catheter sheath 322 (see FIG. 11C) can be retracted, exposing first a distal region of the pump portion. In FIG. 11C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 11D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta ("AA").

Figure 11E:
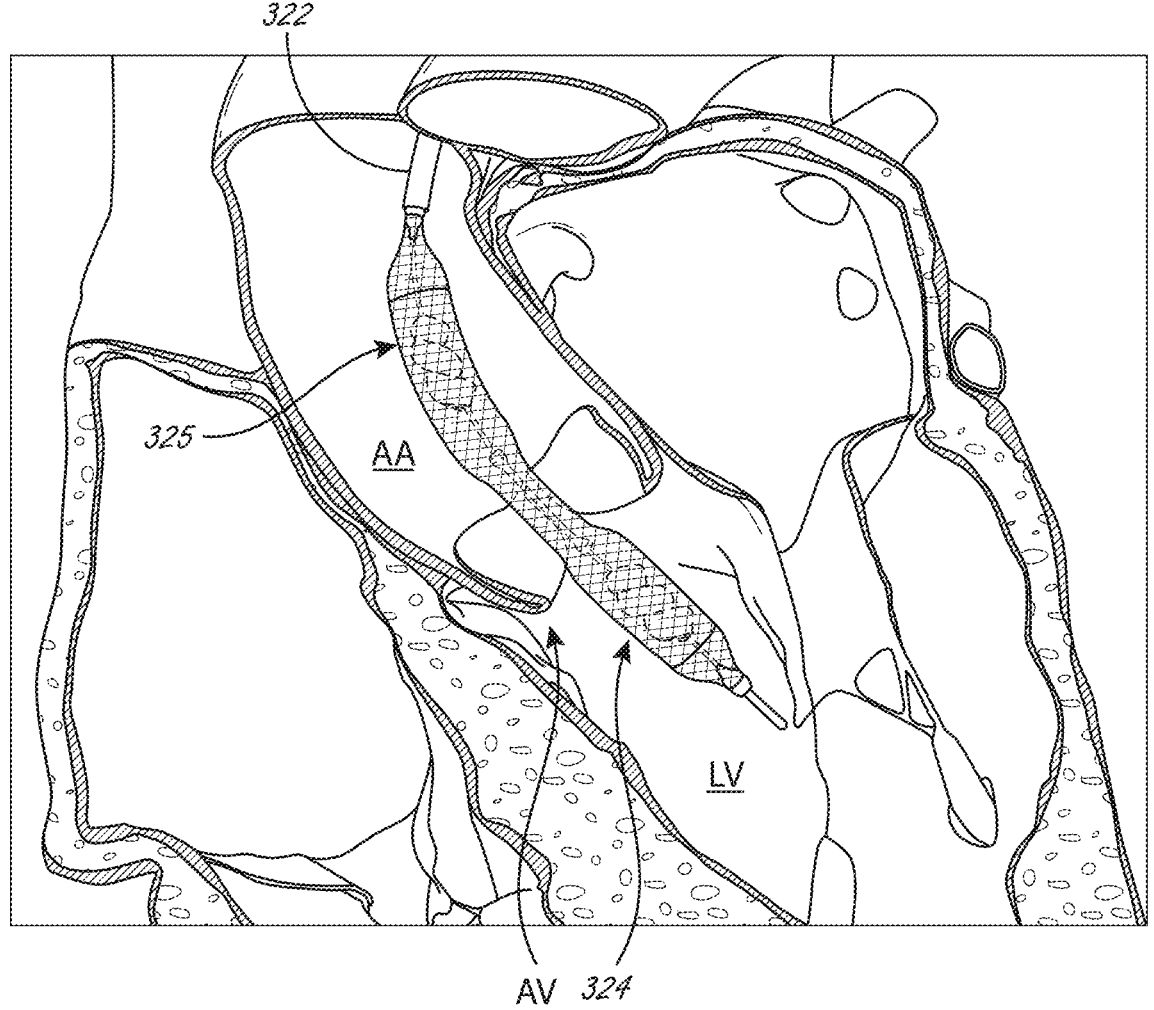
Figure 11F:
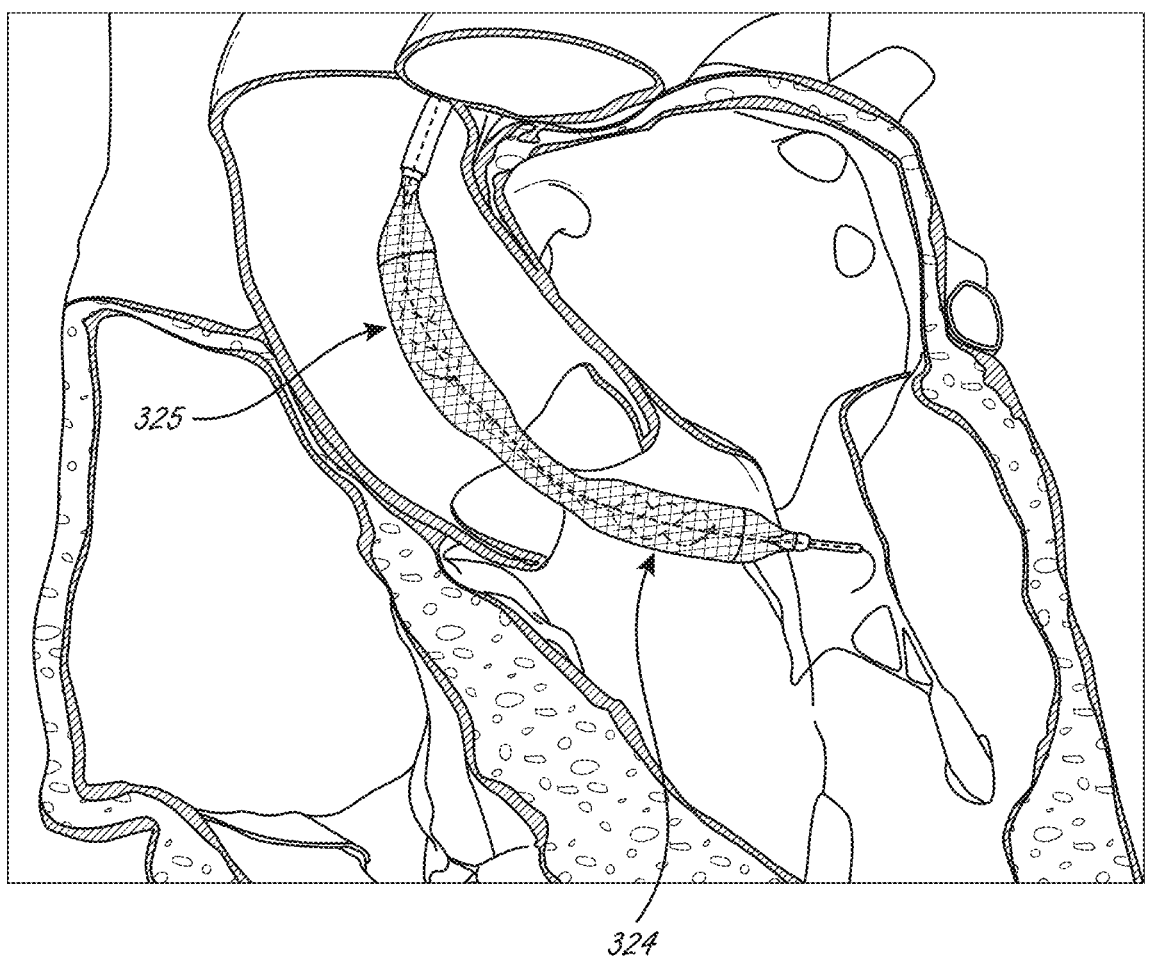

The second wire (e.g., an 0.018" guidewire) may then be moved prior to operation of the pump assembly (see FIG. 11E). If desired or needed, the pump portion can be deflected (active or passively) at one or more locations as described herein, as illustrated in FIG. 11F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. It is understood that in FIG. 11F, the pump portion is not in any way interfering or interacting with the mitral valve, even if it may appear that way from the figure.

Any number of clean and waste fluid pathways or lines may then be coupled to the proximal portion of the blood pump that is disposed outside of the patient. For example, fluid inlet(s) lines and fluid outlet(s) lines in communication with any of the fluid cassettes herein may be attached to one or more fluid ports on the proximal portion of the blood pump. A purge process may then be initiated to move fluid into the blood pump through at least one fluid pathway. One or more confirmation steps can be performed to confirm the purge is operating as intended before turning on the pump. The pump assembly can then be operated, causing rotation of the one or more impellers. Any one of flow rate(s), pressure(s), and motor operation may be monitored at any time.

The disclosure that follows is related to systems, devices, and methods for controlling the delivery of fluid (e.g., purge and/or cooling fluid) through one or more fluid pathways in intravascular blood pumps, some examples of which have been described above. Any of the disclosures that follows may be incorporated into any suitable catheter blood pump herein or its methods of use. In some uses, fluid is delivered to one or more bearings housing and bearings therein, such as any of the proximal bearing and/or distal bearings. Additionally, fluid may be delivered through a delivery sheath pathway out of the delivery sheath, which is described in more detail below.

Figure 12:
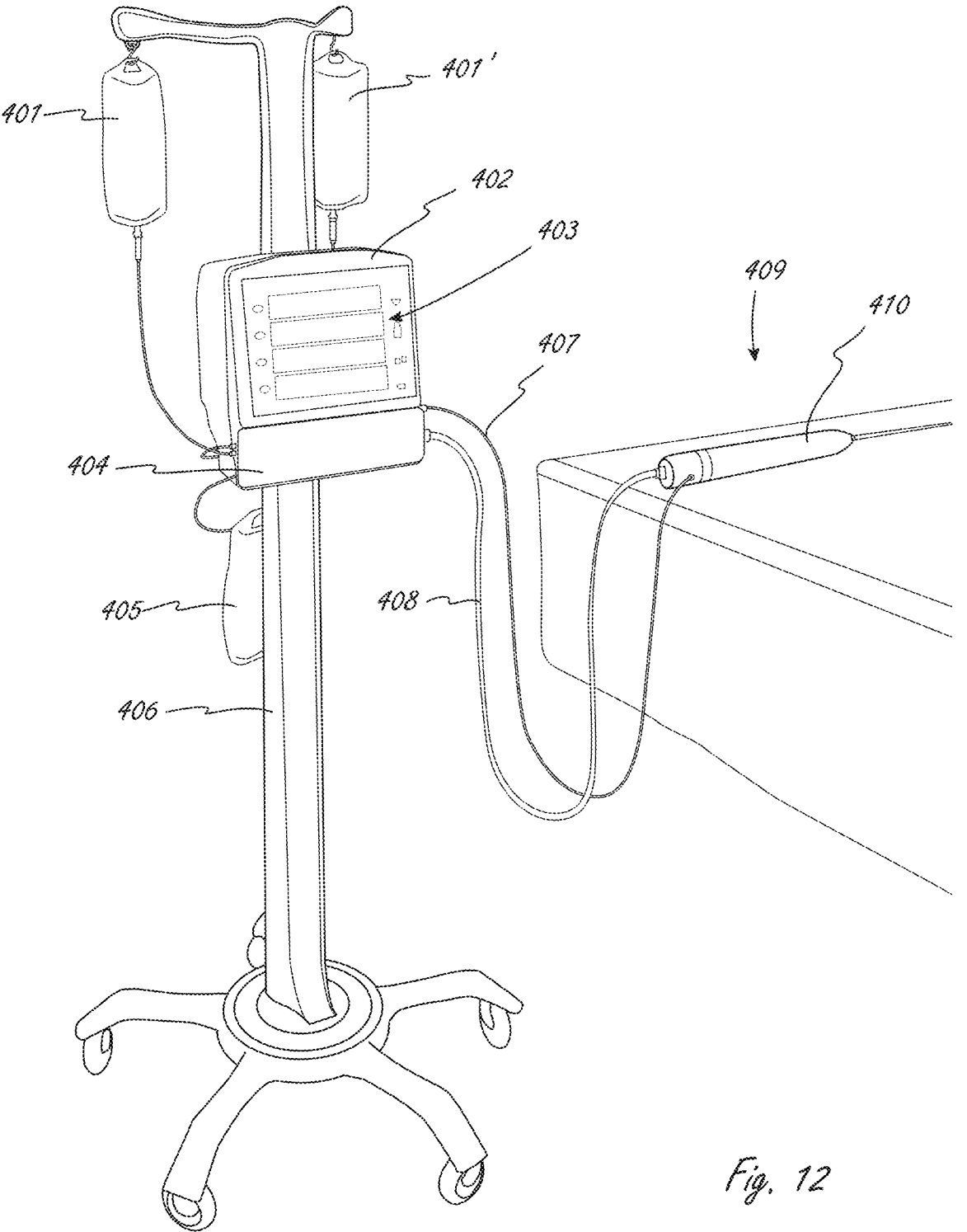
FIG. 12 illustrates an exemplary fluid control system coupled to a intravascular blood pump.

FIG. 12 illustrates an exemplary external fluid control system coupled to and in fluid and electrical communication with a blood pump, which may be any of the blood pumps herein. The external fluid control system includes an external console (which may be referred simply as a console herein) secured to a fluid cassette (which may be referred simply as a cassette herein), which together may be considered part of the blood pump system when they are put into operable communication with the catheter blood pump. Examples of operable communication in this context include fluid and electrical communication. The exemplary external components of the system in FIG. 12 include optional stand 406, which supports console or control unit 402, console touchscreen interface 403, fluid cassette 404 shown coupled to console 402, waste fluid reservoir 405, and fluid input reservoirs 401 and 401' (which optionally may be a single fluid input reservoir). A removable (optionally disposable)

fluidic cassette 404 is adapted to stably interface with console 402 and create one or more fluidic connections between blood pump 409 (which includes handle 410) and both input fluid reservoirs 401 (optionally also 401') and waste fluid reservoir 405. Cassette 404 is configured so that it is removable from console 402, but is configured so that it may be secured to the console for use. Blood pump 409 is also shown in electrical communication with console 402 via electrical connection 407, which can provide energy to activate a motor of the blood pump, examples of which are shown herein. The blood pump 409 is in fluidic communication with fluidic cassette 404 via fluid connection 408 when cassette 404 is coupled to console 402 and to the blood pump, wherein fluid connect 408 may comprise a plurality of separate fluid lines, as is shown in the examples that follow. The fluid lines may be physically secured together, or they may not, and may comprise one or more sections of fluid tubing. Fluid connect 408 may be part of the fluid cassette 404, which connects to blood pump 409 when ready for use, or it may be considered a separate component connected to the fluidic cassette 404 (and optionally also to the blood pump 409) when ready for use. Interface 403 allows a user to control one or more aspects of the console 402 (e.g., pump operating parameters such as pump speed) and/or operation of the blood pump.

Figure 13:
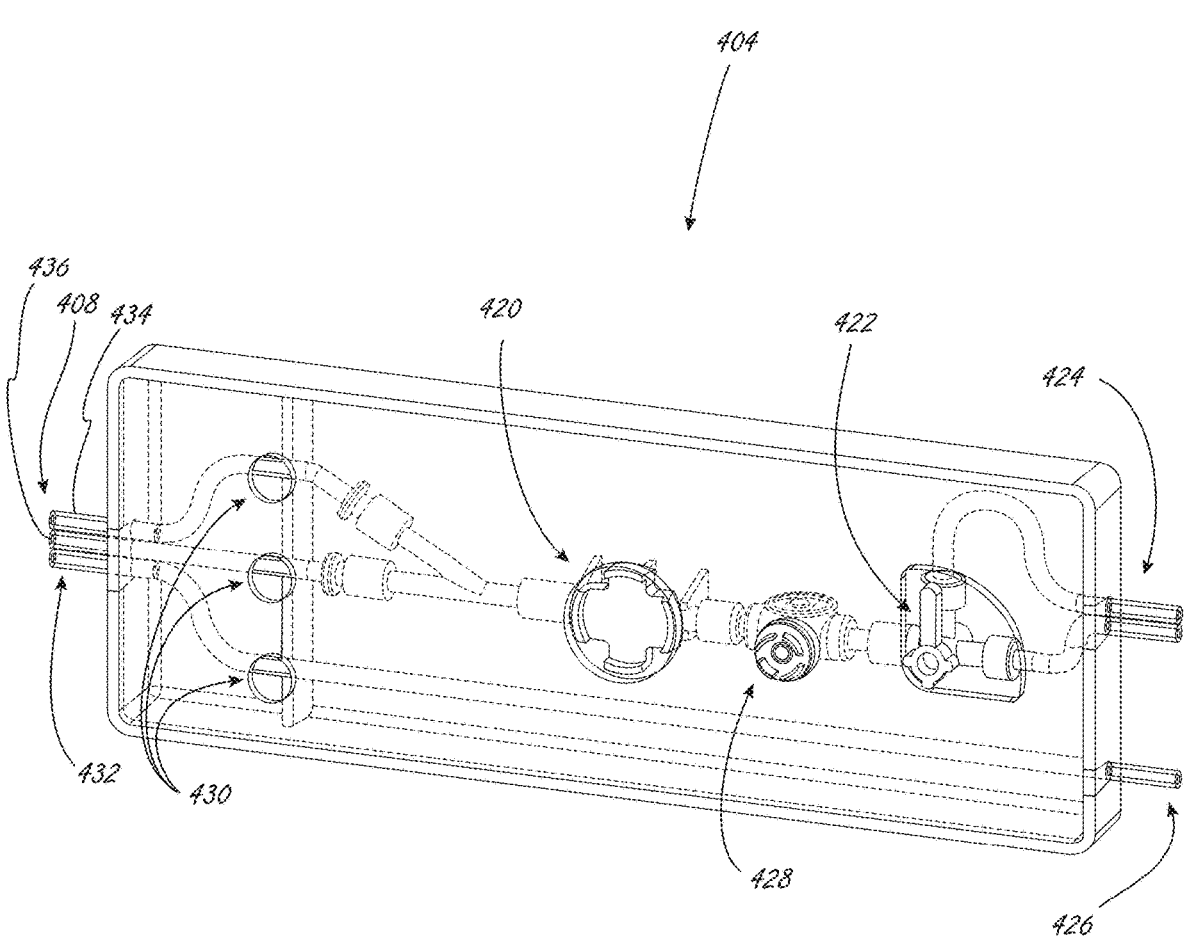
FIG. 13 illustrates an exemplary fluid cassette.

FIG. 13 illustrates an exemplary fluid cassette. FIG. 13 shows an inner side of an exemplary fluidic cassette housing 404, as well as internal components within the cassette housing. The inner side in this example is inserted into and faces toward console 402 when the cassette is coupled to console 402, and as such the external console can interact with (e.g., physically, optically, etc.) one or more components in the cassette when the two are secured together. When cassette 404 is engaged with and in operable communication with console 402, one or more components in the console may interact with the cassette 404 to control fluid flow through one or more fluid pathways in cassette 404, both to the blood pump from clean reservoir(s) 401 and from the blood pump to waste reservoir 405. In this example, fluid from the one or more clean fluid reservoirs enters through first and second fluid inlets 424, selection of which may optionally be made with the optional clean fluid reservoir regulator 422 (e.g., a valve). Fluid may be directed towards the blood pump through fluid outlets 434 and 436, one of which may be in fluid communication with the catheter while the other may be in fluid communication with an outer sheath, where only the catheter pathways returns to the cassette as waste fluid. Return fluid from the catheter may enter cassette 404 at waste or return fluid inlet 432 and flow to waste outlet 426 and on to waste fluid reservoir 405. Sensor 420, which may only be a portion of a pressure sensing mechanism (e.g., a deformable membrane or diaphragm), may facilitate information to be sensed that is indicative of flow or fluid pressure with the fluid pathway. In examples in which the sensor is part of a pressure sensing assembly, the sensor may facilitate a fluid pressure reading in the clean fluid pathway within cassette 404. Fluid outlets 434 and 436, as well as waste fluid inlet, are coupled to or part of/form fluid connection 408 shown in FIG. 12. The cassettes herein generally include a cassette housing, which may comprise one or more housing bodies. The cassette housings herein may be a single unitary component, or they may comprise a plurality of components secured together. For example, any of the cassette housings herein may include two or more shells coupled together to form at least part of a cassette housing. In any of the figures herein, a reference to the cassette may also be a reference to a cassette housing generally. For example, in FIG. 13, the cassette 404 may also be considered as housing 404.

The fluid cassettes herein include one or more fluid pathways. A fluid pathway herein generally refers to a pathway along which fluid may be moved. Fluid pathways may be formed from one or more components, such as one or more sections of tubing, either directly attached or indirectly coupled via one or more intermediate members. For example, the cassette shown in FIG. 13 includes three separate fluid pathways, which in this example extend between cassette inlets and cassette outlets.

With cassettes that have optionally two or more clean fluid inlets 424, optional clean fluid reservoir regulator 422 may be electronical controlled, optionally via feedback, and may control which fluid reservoir is input to the blood pump. Sensor 420 may be part of a proximal pressure sensing mechanism for the blood pump system, and may sense fluid pressure in the system at the location of the pressure sensor along that fluid pathway. Cassette housing 404 may have one or more flow control openings 430 formed therein (or any other kind of aperture or deformable member (e.g., a membrane) that allows physical manipulation of the fluid pathway) through a first side surface (in this example an inner side surface), which allows a flow controller of the external console to physically interface with one or more of the three fluid pathways shown to regulate or control the flow of fluid through the one or more of the fluid pathways. For example only, separate pinch clamps in the console may be individually controlled and activated to move towards and to push against fluid tubing in the different pathways in the cassette to stop fluid flow along any of the fluid pathways. Any other type of interface with the console may be used to independently regulate or control flow in any of the pathways. In some embodiments, the control may include two states, such as flow and no-flow. In some other embodiments, the fluid state may be further controlled by the amount of movement of the flow controller to regulate the flow rate through the fluid pathways. The consoles herein may be sized and configured to receive and interface with a disposable cassette for case of setup, examples of which are shown below.

The fluid control and management system may optionally include optional weigh scales for one or dual saline bags and saline waste. These can be used to monitors bag contents and alert a user for changes, which may be optionally regulated with one or more computer executable methods disposed in the console. The system may be adapted to automatically switch over to or select one bag or the other. One or more scales may be used to measure or monitor purge fluid volume that is infused into the patient. Optional hanging scales may be used to detect a low volume fluid reservoir condition or state, which may be part of a method adapted to automatically assess the remaining volume. One or more hanging scales in this context may be in electrical communication with the console. One or more hanging scales may be used for the waste reservoir as well, such as to verify flow or detect a full waste reservoir.

The fluid control and management system may optionally be adapted with distributed flow control to ensure proper lubrication and cooling of all drive components. In the example shown in FIG. 13, flow through each of the individual fluid pathways may be separately and individually controlled as desired by providing access to each pathway with the different openings 430 in the cassette, as shown. The ability to control flow through the different pathways is a significant improvement that allows much finer control of where fluid is delivered with the catheter, compared to systems that simple turn on a flow of fluid and let it return. Being able to control flow in the waste fluid line and the clean fluid line allows a much finer control of pressure in the catheter, which allows for much better control of where in the catheter fluid is being delivered. For example, if is desired that more fluid flows to a proximal bearing or a distal bearing, or that pressure be increased or maintained at one or more particular locations, the console can close off flow in any desired pathway independently of the other to facilitate fluid delivery and/or pressure control to the one or more desired locations in the catheter.

As set forth above, the console may include one or more valves (such as pinch valves) that, when the cassette is engage with the console, facilitate control of flow through the one or more fluid pathways by mechanically compressing any individual fluid pathway to stop or slow the flow of fluid, or releasing them to allow or increase flow through the one or more pathways. For example, if it is desired to increase pressure in the waste or return pathway, the flow of fluid through the waste pathway (between waste inlet 432 and waste outlet 426) may be slowed or stopped, such as by engaging a console flow controller (e.g., pinch valve) with waste pathway tubing through the corresponding waste opening 430 to compress the tubing in the waste pathway. Additionally, for example only, fluid flow to the sheath may be controlled separately and independently from the catheter fluid pathways by using different flow controllers in the console (e.g., pinch valves) to control fluid flow to the different fluid outlets 434 and 436. While not shown, in alternative examples the waste pathway may also include a sensor (e.g., pressure sensor) associated therewith to sense flow or pressure along the waste fluid pathway, which may be used as part of a method to verify waste flow back from the blood pump. In embodiments in which fluid connect 408 is a separate component from the cassette, fluid connect 408 may be connected with the cassette before or after the cassette is engaged with and secured to the console.

In any of the embodiments herein, fluid connect 408 may be part of the cassette and is considered part of the cassette pathways. In these example, the fluid connect 408 is considered to include the cassette fluid inlets and outlets.

One of the cassette fluid outlets, such as clean fluid outlet 436, may be fluidly connected so as to deliver fluid to a sheath fluid pathway, while clean fluid outlet 434 may deliver fluid to an internal fluid pathway of the blood pump catheter. Outlet 436 may be considered part of a sheath fluid pathway, and outlet 434 may be considered part of a catheter fluid pathway.

In some embodiments, optional regulator 422 may be an automatically controlled valve adapted to switch between optional plurality of fluid input reservoirs.

In some embodiments pump 428 may be a pulsatile pump to provide flow, and may be driven by a stepper motor. In some embodiments the pump may be configured to operate from one to three speeds, for example, without a speed feedback loop.

Sensor 420 (which may be part of a sensing subassembly) may be used to detect blockages and/or overpressure conditions. For example, information sensed from sensor 420 may be used by one or more computer executable methods stored in the console to automatically detect operating conditions of the pump.

Figure 14A:
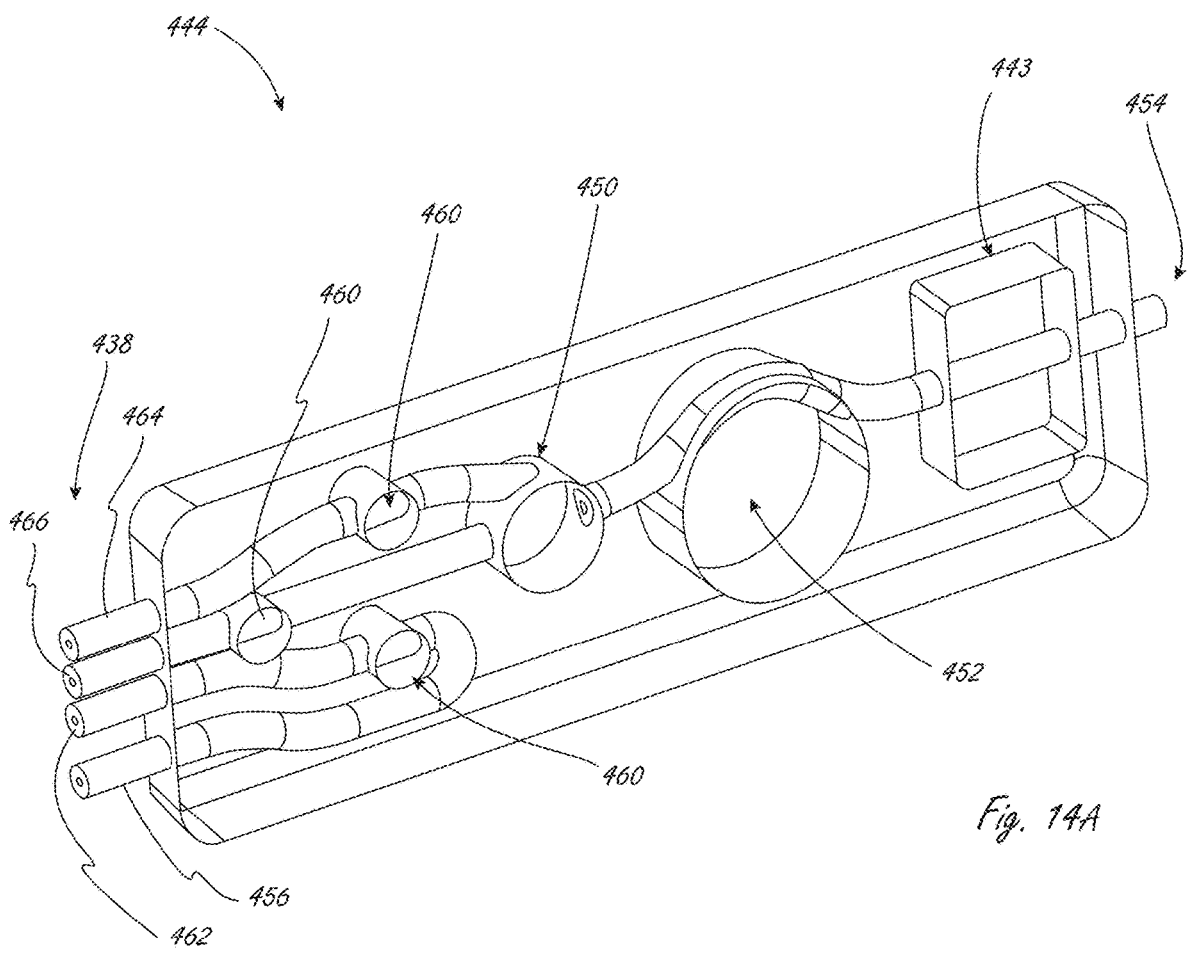
FIGS. 14A and 14B illustrate an exemplary fluid cassette.
Figure 14B:
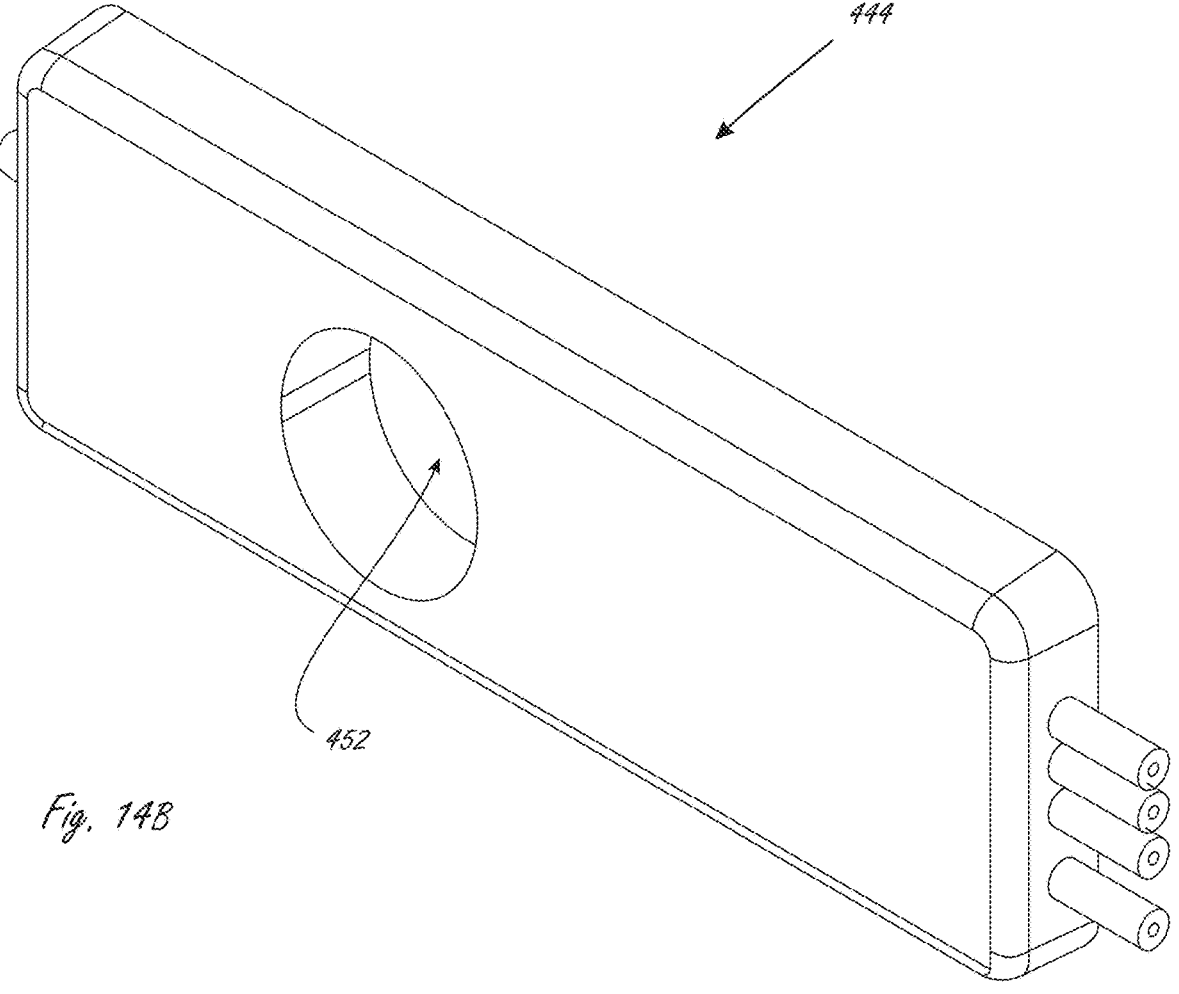

FIGS. 14A and 14B illustrate an exemplary cassette 444 (also referring to the cassette housing generally) that may incorporate any suitable features of cassette 404 or any other cassette herein. In this example, there is a clean fluid inlet 454, and wherein the fluid pathway passes through optional bubble detector region 463. Cassette 444 includes pump head receiving area 452, which is an aperture in this example and sized to receive a pump herein (e.g., peristaltic pump with rollers) therein, examples of which are described below. Cassette 444 may also include sensor portion 450 (e.g., a deformable membrane) in line with the fluid pathway, as shown. Cassette 444 includes sheath fluid outlet 464 and catheter fluid outlet 466, as well as waste pathway inlet 462 and waste pathway outlet 456 which carries fluid to a waste reservoir (not shown). FIG. 14A shows an inner surface of the cassette and internal components, and FIG. 14B shows an external surface but does not show internal components. Cassette 444 includes flow control openings 460 that are configured to provide individual access to the fluid pathways, as is described above with reference to FIG. 13. Any disclosure thereof is incorporated by reference into the example in FIG. 14. The flow control openings 460 allow flow controllers in the console to interface with the fluid pathways as is described with reference to FIG. 13 to control (e.g., stop flow, decrease flow, start flow, increase flow) the flow of fluid through any of the fluid pathways. Pump receiving area 452 may receive a pump with rollers therein that interface with the fluid pathway shown and cause fluid to flow therethrough.

In the example in FIGS. 14A and 14B, there are two clean fluid pathways in the cassette, both having the same inlet 454, but having different fluid outlets 464 and 466. The two pathways are considered the same upstream (to the right in the figure) of the bifurcation, which in this embodiment is proximate the sensor 450 location. The two pathways diverge at the bifurcation. In this example, the pump and sensor are upstream to the bifurcation.

In the example in FIGS. 14A and 14B, outlets 464 and 466 are on a common side or surface of the cassette housing, and inlet 454 is on a second side of the cassette housing that is spaced from the first side. In this example, the waste line inlet 462 is on the same side as the outlets 464 and 466. Waste outlet 456 may also be on the same side, as shown in FIG. 14B, or it may be on a different side such as in the embodiment in FIG. 13.

In some embodiments, bubble detector region 443 may be configured to receive therein a light source (e.g. LED) on one side of the fluid pathway and a detector on the other side, together configured to detect bubbles in the fluid pathway when the cassette is secured to the external console. Bubble detector region 443 may be sized and configured to receive an ultrasound bubble detector therein in some embodiments.

Sensor 450 may be a portion of a pressure sensor and may include a diaphragm, which is adapted to interface with a load cell in an external console, which can detect deformation of the diaphragm, which may be indicative of the fluid pressure within the fluid pathway.

In any of the embodiments herein, the console may include linear actuators that are driven by, for example, stepper motors, configured to be advanced into contact to push or compress on the fluid pathways to stop or slow flow through the fluid pathways. Other mechanisms may be implemented for stopping and starting flow through the pathways.

Exemplary cassettes herein may include a part of a sheath fluid pathway. In the examples herein, the sheath fluid pathway does not return as part of the waste or return pathways. Fluid pumped to the sheath passes out into the patient, which may be used to prevent blood from clotting. The waste or return pathways herein are generally from the catheter.

FIGS. 15A-18 illustrate features of exemplary cassette/console interactions, which may facilitate a console pump to be able to cause fluid flow in one or more cassette fluid pathways.

Figures 15A, 15B:
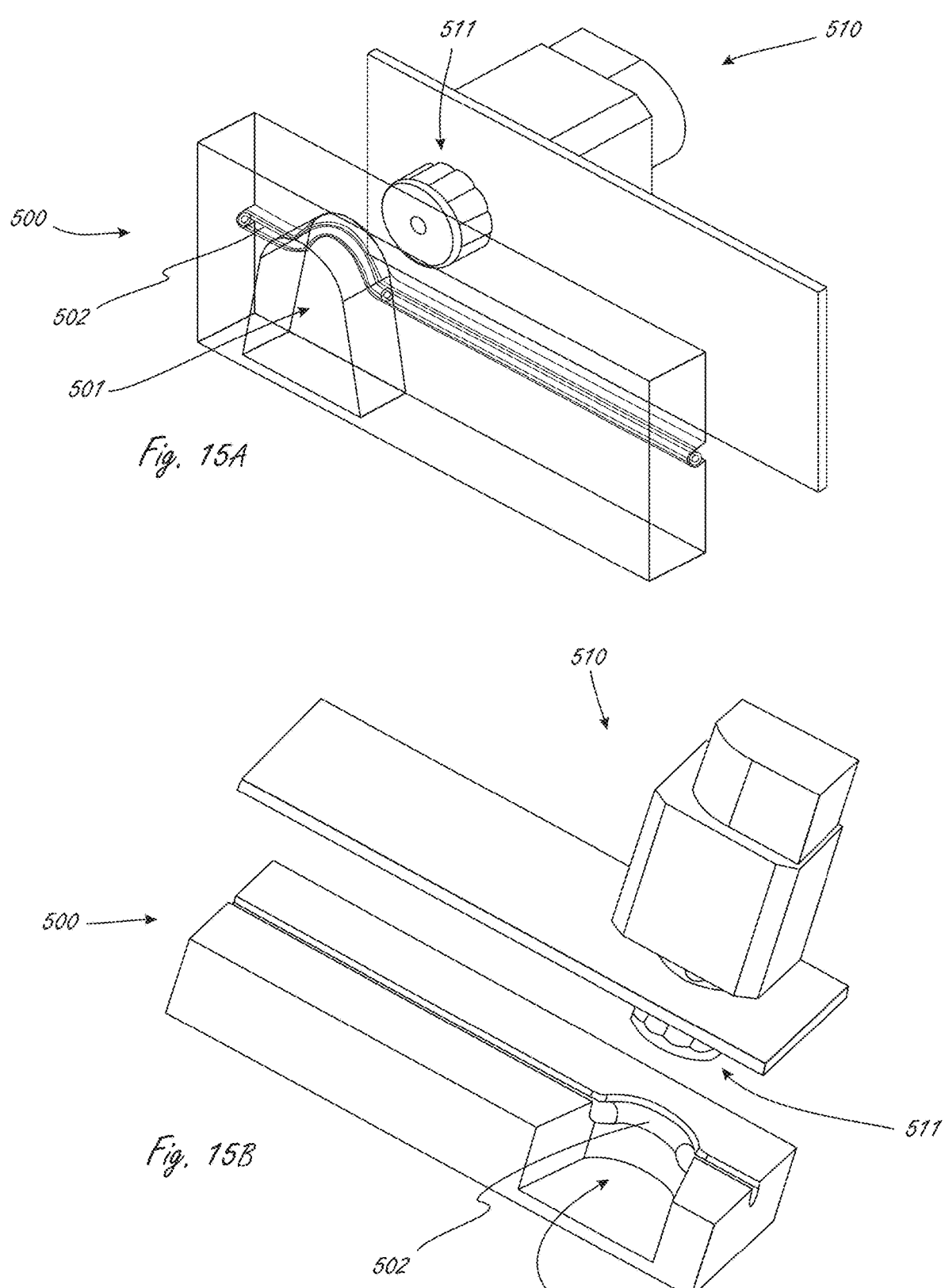
FIGS. 15A and 15B illustrate exemplary interactions between a portion of exemplary cassette and a portion of an external console.

FIGS. 15A and 15B illustrates cassette 500 and at least a portion of pump 510, which may be part of any of the consoles herein. Pump 510 includes rollers 510, which are configured to roll and cause fluid to move within fluid pathway 502. Cassette 500 includes fluid pathway 502 and pump receiving area 501, which is configured to receive roller portion 511 of the pump therein to interface with line 502. After rollers 511 are positioned in area 501, a separate mechanism within the console may move the rollers against the line, after which the pump may be operated to move fluid within fluid pathway 502.

Figure 16:
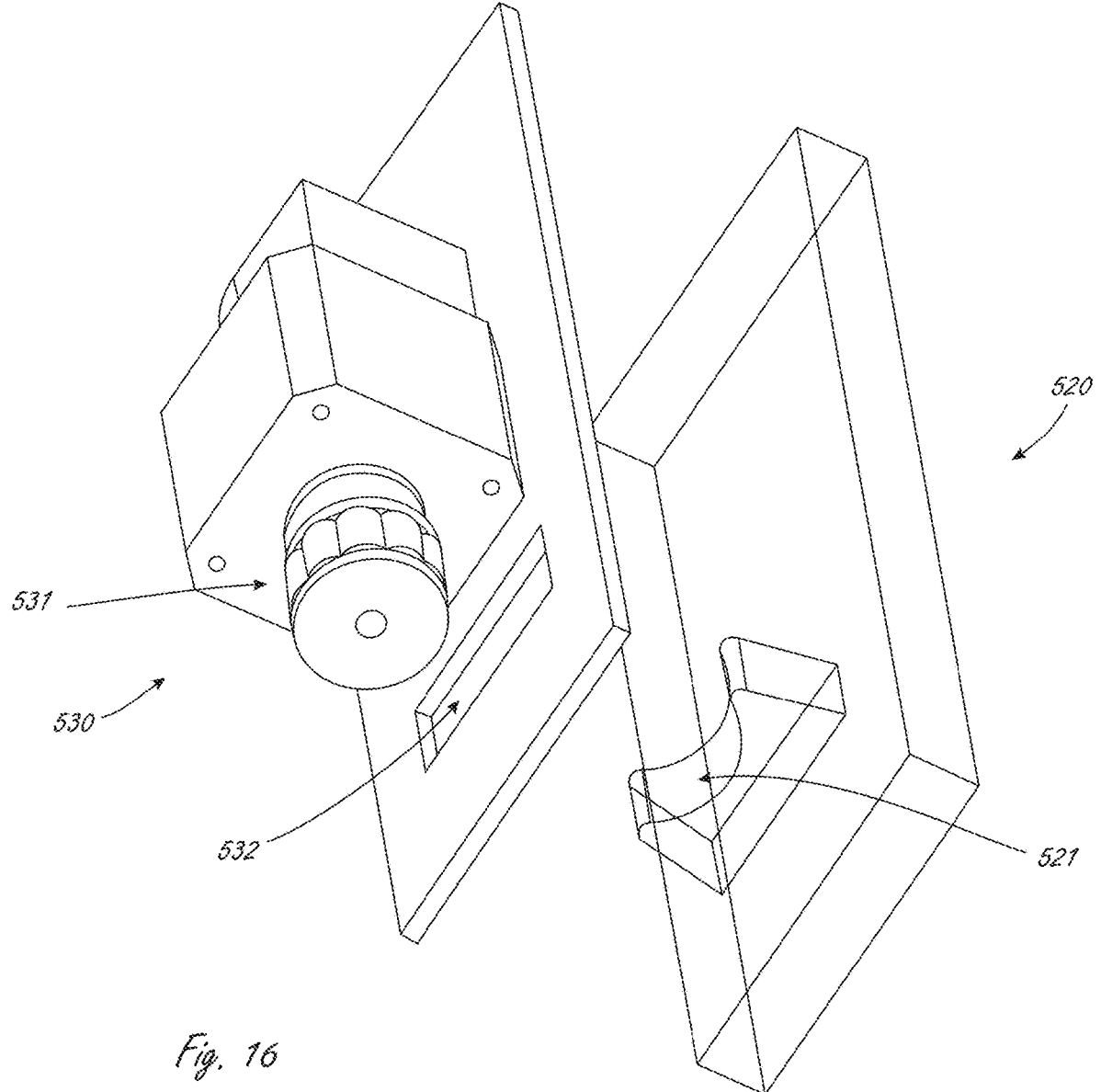
FIG. 16 illustrates an exemplary interaction between a portion of an exemplary cassette and a portion of an external console.

FIG. 16 illustrates a portion of exemplary cassette 520 with a fluid pathway surface 521 on which a fluid line (not shown) would be disposed. Pump 530 includes rollers 531 and aperture 532, through which surface 521 may be advanced to facilitate engagement with rollers 531 and the fluid pathway tubing.

Figures 17A, 17B:
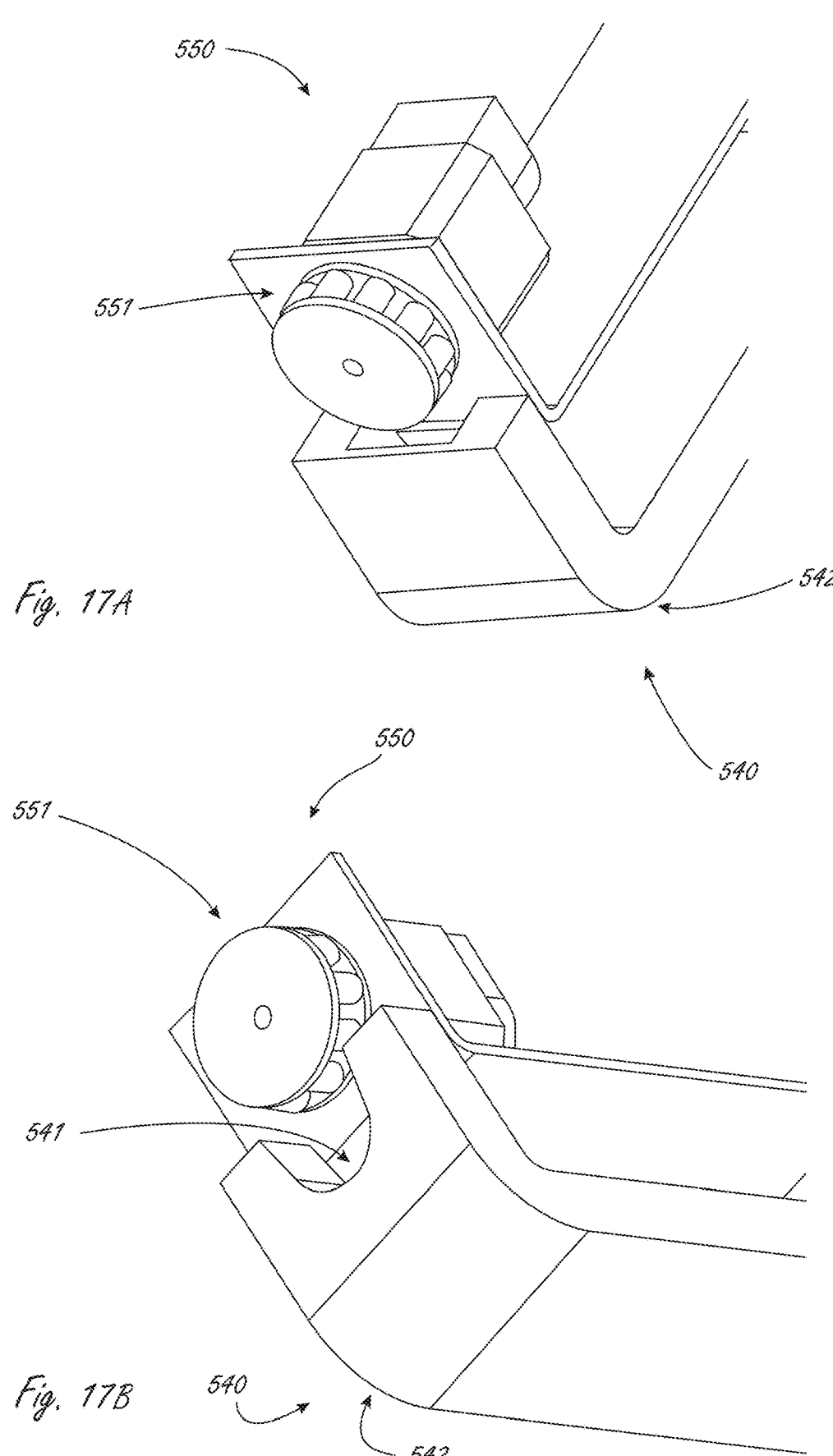
FIGS. 17A and 17B illustrate exemplary interactions between a portion of an exemplary cassette and a portion of an external console.

FIGS. 17A and 17B illustrate an exemplary interaction between cassette 540 and pump 550. Cassette includes a bend 542 formed therein, forming a L configuration at one end of the cassette. Cassette 540 includes a pump receiving area 541, which is at one end of the cassette and is configured to receive rollers 551 therein. Cassette 540 includes a fluid pathway, which is not shown, but which would be disposed in pump receiving area 541.

Figure 18:
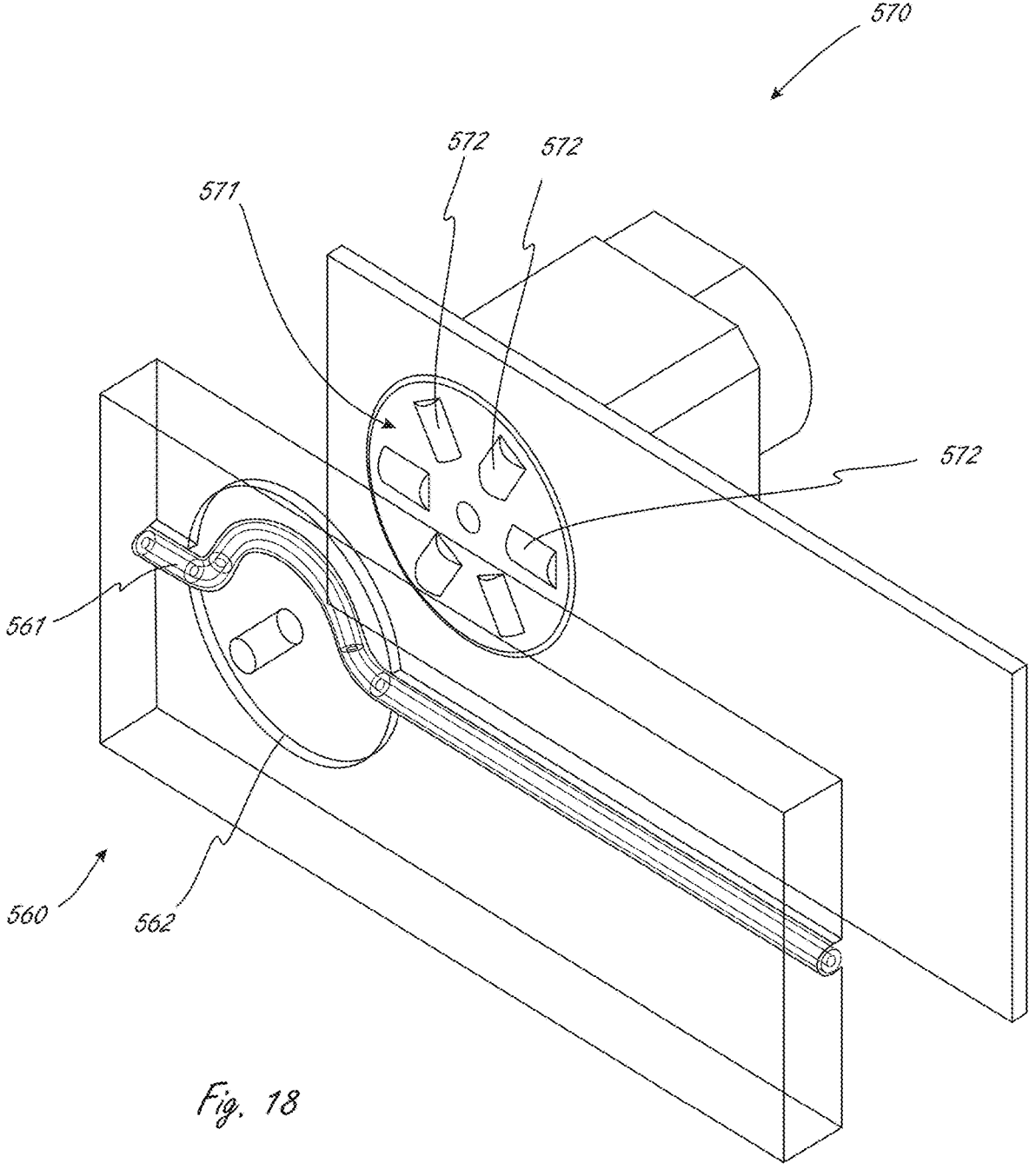
FIG. 18 illustrates an exemplary interaction between a portion of an exemplary cassette and a portion of an external console.

FIG. 18 illustrates exemplary cassette 560 and pump 570, which includes rollers 572. Cassette 560 includes a circular depression 562 and fluid line 561. When cassette 560 is moved toward pump 570, rollers 572 may interface with fluid line, after when the pump may be activated to cause fluid to flow within fluid pathway 561.

Figure 19A:
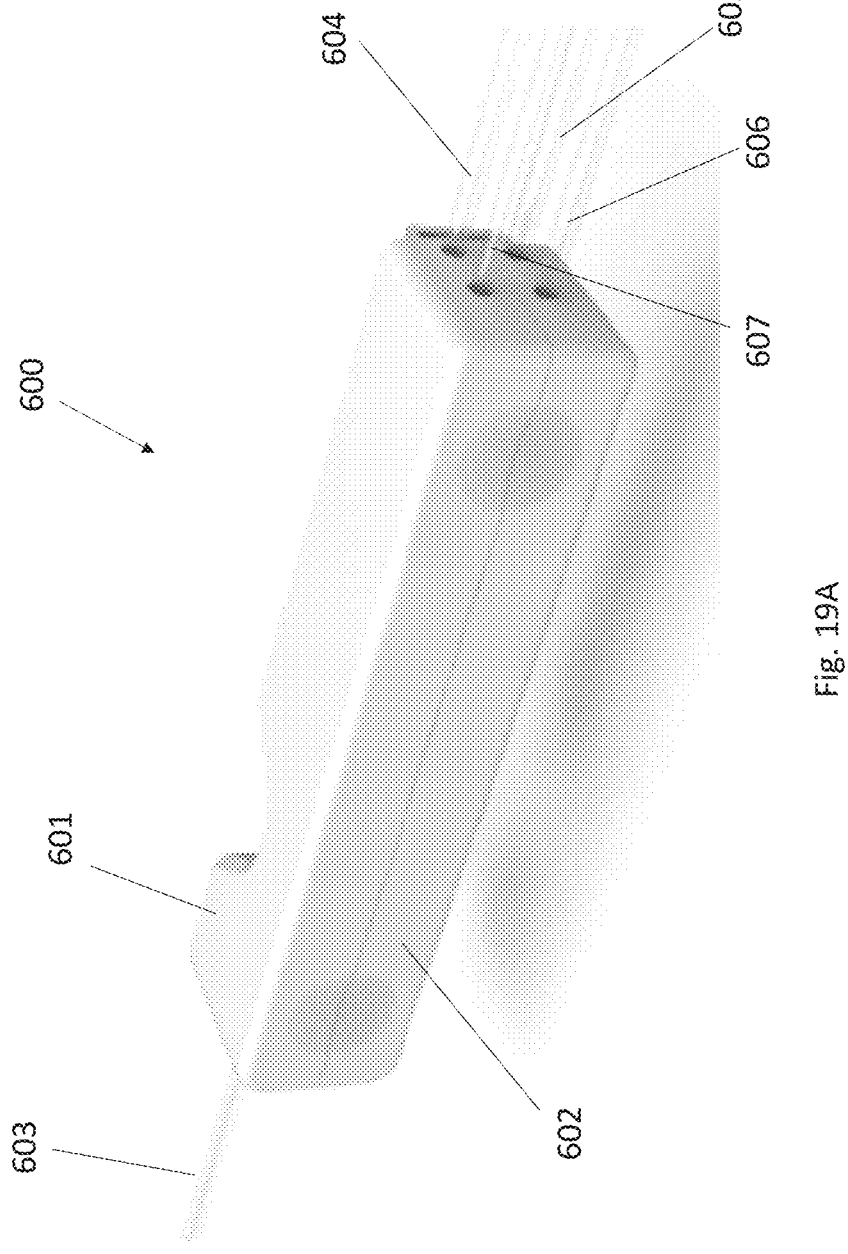
FIGS. 19A-19D illustrate an exemplary embodiment of a fluid cassette.
Figure 19B:
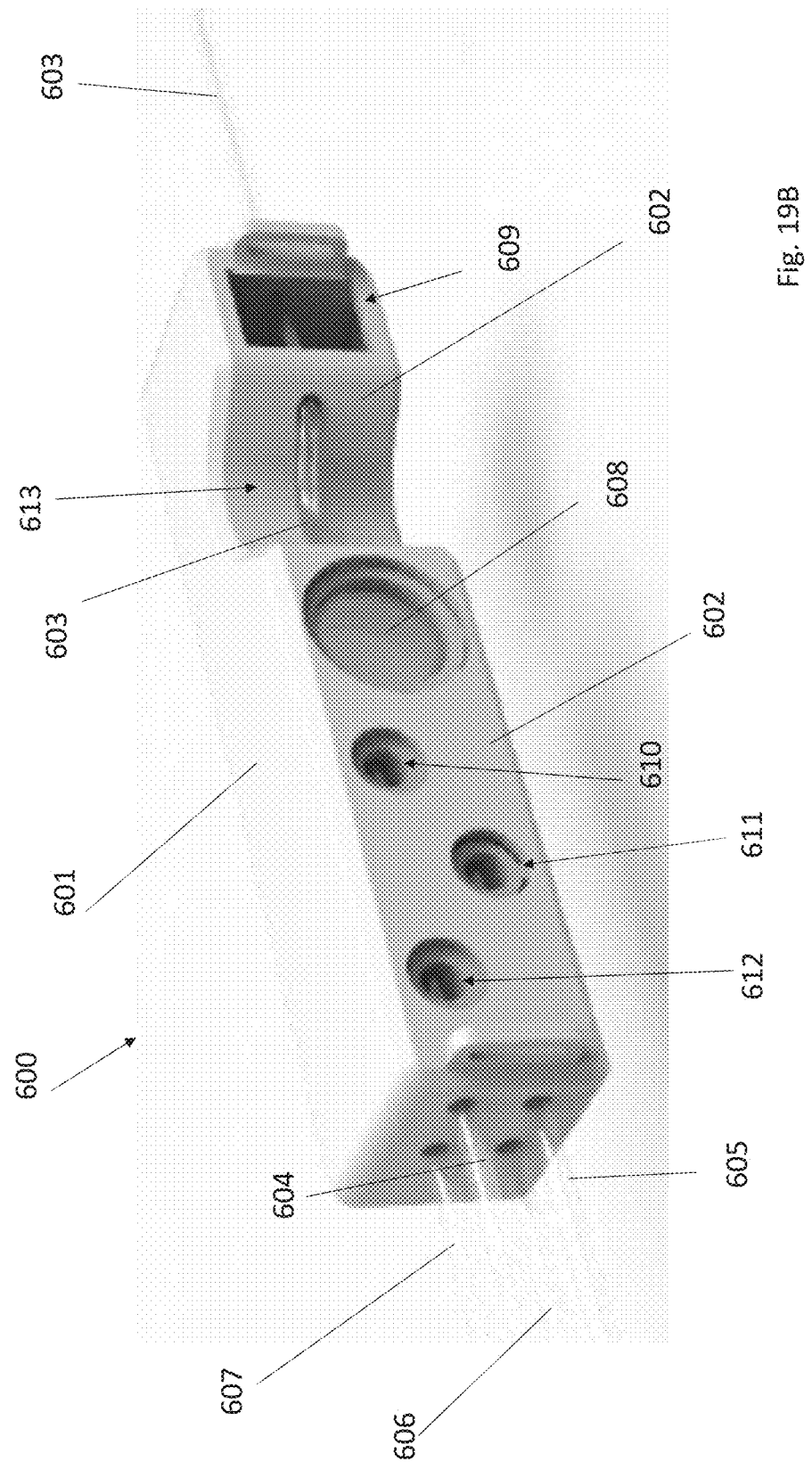

FIGS. 19A-19D illustrate an exemplary cassette in which the cassette housing includes an inner fluid control subassembly within one or more outer cassette shell components. FIG. 19A illustrates an outer perspective view of cassette 600 in an assembled configuration, and FIG. 19B illustrates an inner perspective view of cassette 600. Cassette 600 includes first outer shell 601 and second outer shell 602, which together comprise a portion of the outer surfaces of the cassette housing. Cassette 600 includes clean fluid tubing 603, which is configured to be in communication with fluid from a clean fluid reservoir. Cassette 600 includes catheter fluid outlet tubing 607, which is adapted to be in fluid communication with a catheter. Cassette 600 includes sheath fluid outlet tubing 604, which is adapted to be in fluid communication with a sheath. Cassette 600 includes waste fluid inlet tubing 605 and waste fluid outlet tubing 606, which is adapted to be in fluid communication with a waste fluid reservoir.

FIG. 19B illustrates an inner perspective view of cassette 600. The inner view shows opening or aperture 610, which allows for console control of the fluid in the sheath fluid tubing 604, opening or aperture 612 which allows for console control of the fluid in catheter fluid outlet tubing 607, and opening or aperture 611, which allows for console control of the fluid in the waste fluid tubing. Console control of the fluid within these pathways may be the same as is described with respect to the FIGS. 13 and 14A and 14B.

Figure 19C:
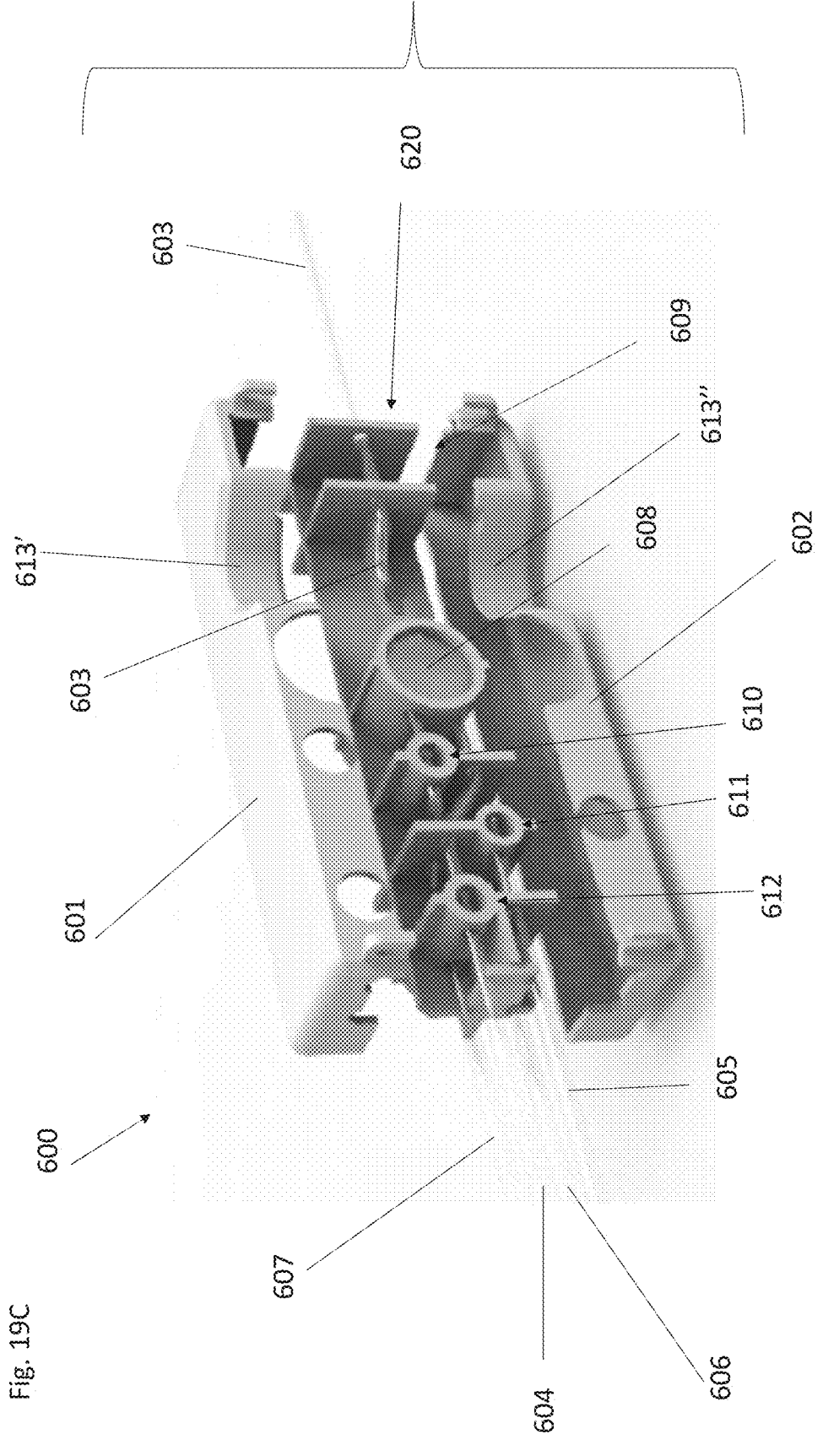
Figure 19D:
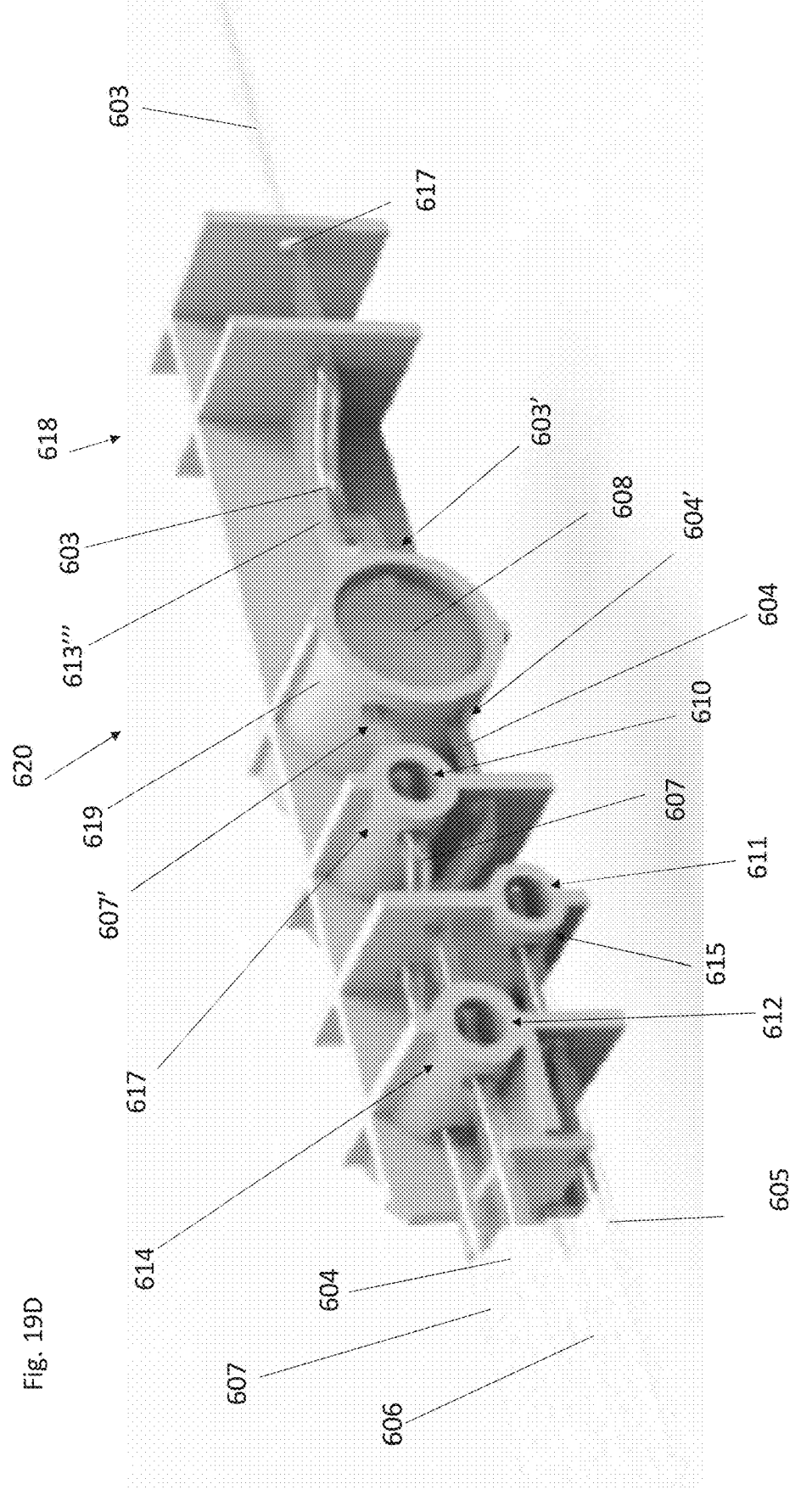

FIG. 19C illustrates an exploded view of cassette 600, showing shell 601 and shell 602 displaced up and down, respectively, from their assembled configuration in FIGS. 19A and 19B, to illustrate an exemplary inner subassembly 620, which is also shown by itself in FIG. 19D. The inner subassembly 620 includes an inner body 618. The inner subassembly in this example may include the inner body 618, the fluid pathways in the cassette, as well as a portion of a pressure sensor 608. The inner body includes openings through which the tubing of the fluid pathways pass, which can be seen in FIG. 19D. For example, with reference to FIG. 19D, clean fluid tubing 603 passes through aperture 617 and into inner body 618, and follows curved surface 613''' of the inner body as shown. The curved surface 613''' comprises the pump head receiving area of the cassette, which is positioned to engage with pump head rollers when the cassette is engaged with the console, which is described in more detail herein. Clean fluid tubing 603 then interfaces with pressure sensor housing 619, which may house therein a portion of a pressure sensor 608, such as a diaphragm that is configured and positioned to interact with the console to thereby communicate changes in fluid pressure within the housing 619 as fluid flows therethrough. In this example, the catheter fluid outlet tubing 607 is coupled to pressure sensor housing 619 at location 607', and after the path deviates laterally in the FIG. 19D as shown, exits the inner body 618 as shown. Sheath fluid tubing 604 is also coupled to and in fluid communication with pressure sensor housing 619, and as shown deviates up and then exits the inner body 618. The clean fluid pathway thus includes a bifurcated pathway, similar to the design in FIGS. 14A and 14B. Downstream to the pressure sensor area (to the left in the figure), one pathway 607 deviates laterally (side to side), and one pathway 604 deviates up and down.

As shown in FIG. 19C, the shells 601 and 602 include openings that are positioned to overlap with the apertures 610, 611 and 612 to allow access to the fluid pathways therethrough by the flow controllers in the console.

Cassette 600 includes bubble detector region 609 that is sized and configured to interface with a bubble detector disposed in the console, examples of which are described herein.

The cassettes herein may include a portion of a pressure sensor, which may include a flexible membrane of diaphragm. The consoles herein may include a second portion of the pressure sensor, such as a load cell configured to interface with a membrane or diaphragm, and which is adapted to be responsive to flexing of the diaphragm which occurs in response to changes in fluid pressure. The load cell may be in communication with one or more computer executable methods stored on the console that are configured to regulate one or more functions of the pump in response to the sensed pressure in the clean fluid pathway in the cassette, examples of which are described herein.

Shells 601 and 602 also have curved surfaces 613' and 613" (concave in this example) that form part of the pump head receiving area.

As shown in FIG. 19D, inner body 618 includes a tubing passthrough 614, through which tubing 604 and 607 pass. Tubing passthrough also defines aperture 612, which provides physical access to tubing 604 therein to control the flow of fluid therethrough. Inner body 618 also include waste tubing passthrough 615, through which the waste fluid tubing passes, and which also defines aperture 611 which provides physical access to tubing 605 therein to control the flow of fluid therethrough. Inner body 617 also includes sheath fluid tubing passthrough 614, through which sheath fluid tubing 607 passes, and which defines aperture 610 which provides physical access to tubing 607 therein to control the flow of fluid therethrough.

Figure 20:
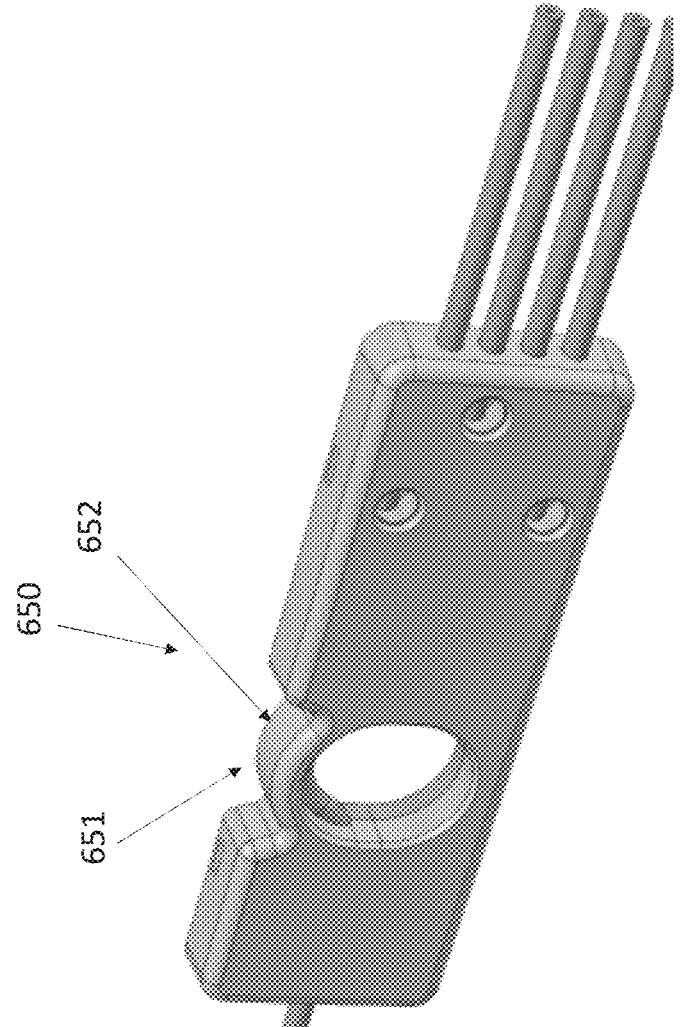
FIG. 20 shows an external perspective view of an exemplary fluid cassette.

FIG. 20 illustrates a perspective outer view of an exemplary cassette 650, which may have any of the same features as cassette 444 shown in FIGS. 14A and 14B. For example, the fluid pathways in cassette 650 may be the same as cassette 444. Cassette 650 includes depression or cutout region 651, which includes curved surface 652, which is shaped to mate with a surface of a console door, additional details of which are described below.

Figures 21A, 21B, 21C, 21D:
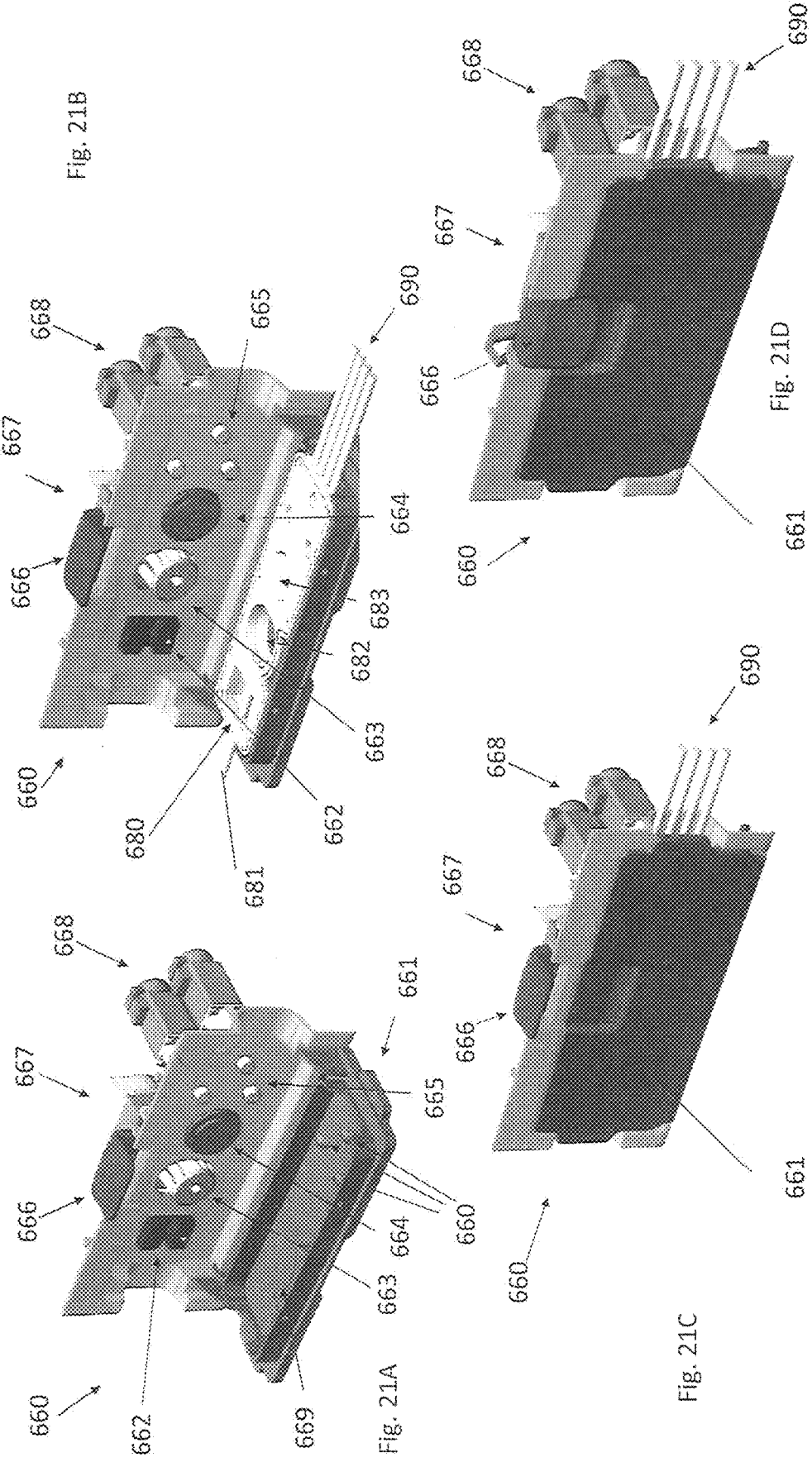
FIGS. 21A, 21B, 21C, 21D, 21E, 21F, 21G, and 21H illustrate an exemplary portion of an external console, and an exemplary fluid cassette.

FIGS. 21A-21H illustrate a merely exemplary mechanism by which an exemplary cassette may be engaged with and put into operable communication with an exemplary external console to control the flow of fluid through the cassette and the intravascular blood pump. It is of note that this is merely an exemplary console and cassette and an exemplary manner by which they can be put into operable communication. FIGS. 21A-21H illustrate an exemplary console 660 that includes a door 661 that is adapted to be moved between an open configuration as shown in FIG. 21A and a closed configuration, such as shown in FIG. 21C.

Cassette 680 and door 661 are both configured such that when the cassette 680 is loaded into the door 661 as shown in FIG. 21B, the cassette and console interface and engage so that the cassette is secured relative to the console in at least one direction.

Door 61 includes one or more features extending from an inner surface thereof that are configured to interface with one or both of the cassette and other console components. In this example, cassette 680 includes curved surface 652 as shown in FIG. 20, which is shaped to mate with curved surface 669 on door 661. The curved surface 669 in the door is disposed to receive forces applied by the pump rollers when in use. This allows the cassette to have a cut out region as shown, which does not require the cassette to be as rigid in this region, which allows less cassette material to be used and thus may decrease the cost of the plastic used in the cassette. The door is part of the reusable console, while cassettes herein may be disposable and thus are preferably cost effective to manufacture. Additionally, the exemplary door 661 includes three wedges 660, which are each positioned to act as a backstop to the linear force applied by linear actuators 668, which act to compress the three individual tubes in this example. Each section of tubing is thus compressed between a flatted end of a linear actuators and a wedge 660.

Console 660 also includes pump head 663 (which may be referred to generally as a pump herein), which may be a peristaltic pump with rollers as shown. Pump head 663 is coupled to motor 667. Pump head 663 is sized and configured to be received within pump head receiving area 682 in cassette 680, other examples of which are shown herein.

Console 660 also includes a part of the pressure sensor, such as a load cell 664, which is described in more detail herein, and may interface with diaphragm or membrane 683 that may be part of cassette 680.

Figures 21E, 21F:
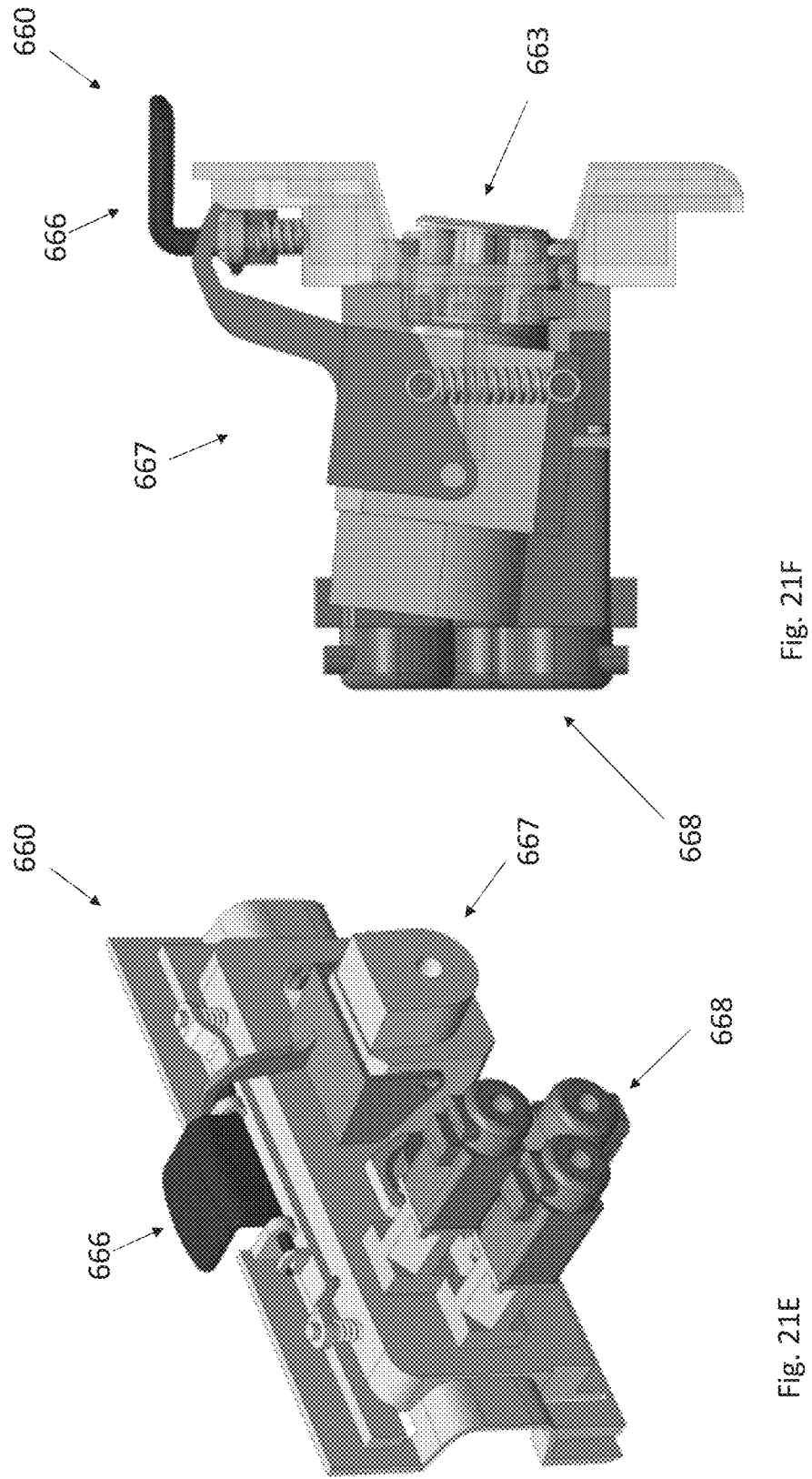
Figure 21H:
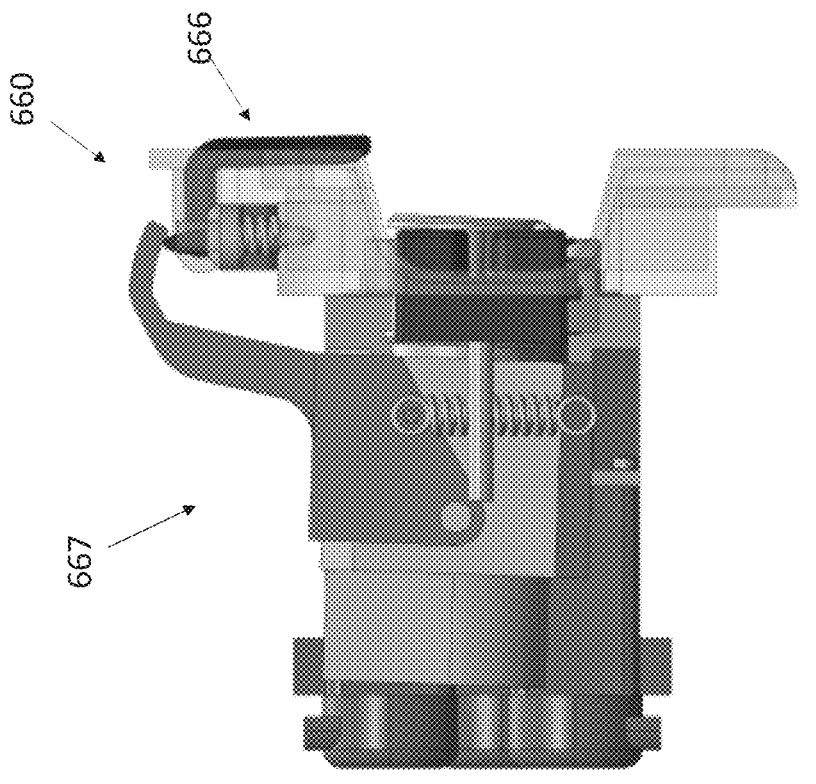
Figure 21G:
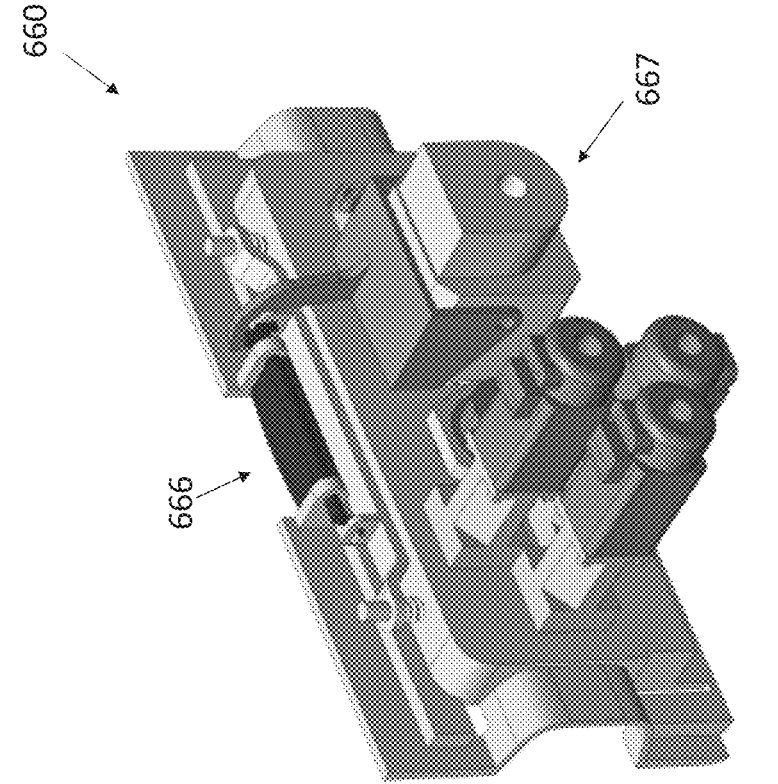

FIG. 21C shows door 661 in a closed configuration. In this state the pump is not operational because the pump head is not interfacing with the clean fluid inlet tubing 681. FIGS. 21E and 21F also illustrate the state of console when the door (not shown) is closed. As most easily seen in FIG. 21F, the pump head and motor assembly is slightly angled relative to a front face of the console (in this embodiment slightly downwardly angled). In this configuration the rollers will not engage with the clean fluid tubing. FIGS. 21D, 21G and 21H show views after latch 666 on the console has been moved to a second locked state, which both secures door 661 in the closed state and also causes movement of the pump head such that the rollers are interfaced with the tubing (e.g., at least partially compressed). In the state shown in FIGS. 21D, 21G, and 21H, when the pump motor

667 is activated, movement of the pump rollers will cause fluid to move though the clean fluid tubing. When latch 666 is pulled downward, the axis of the pump head is moved to position more orthogonal to a front face of the door and/or cassette. In this embodiment, door 661 may fold down about 90 degrees from its closed state, as shown in FIGS. 21A and 21B. While in this embodiment the motor is rotated into an operational position, in other embodiments the motor could be translated up or down as the latch (or other locking mechanism) is closed to cause the rollers to engage the tubing.

Bubble detector 662 may be any known or suitable type of bubble detector, such as ultrasound or optical based.

Linear actuators herein may be in communication with and driven by stepper motors (shown generally as 668 with the linear actuators), for example. As is set forth herein, the linear actuators may be independently controlled and activated as might be desired to control the flow through any of the fluid pathways individually or in combination with each other.

The disclosures includes fluid control systems for an intravascular blood pump, wherein the systems may include any of the external controllers herein and any of the cassettes herein, including their use.

FIGS. 22A-25D illustrate merely exemplary consoles and fluid cassettes, and illustrate exemplary configurations for each that facilitate the cassette engaging the console and being put into operable communication therewith. The cassettes set forth or shown in FIGS. 22A-25D may be modified with features of other cassettes herein and used with the same console that is shown.

Figures 22A, 22B, 22C, 22D:
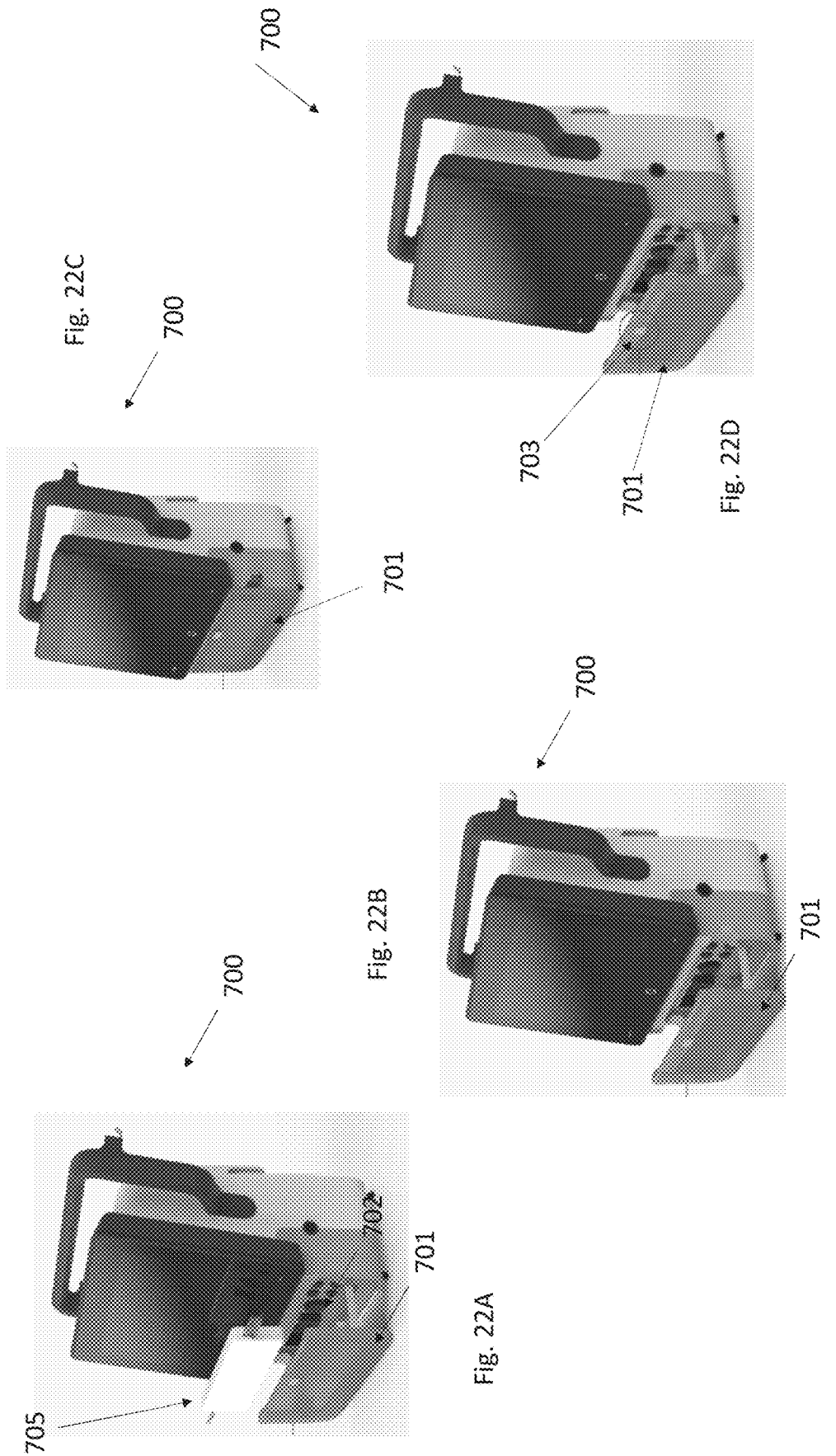
FIGS. 22A, 22B, 22C, and 22D illustrate an exemplary external console and an exemplary fluid cassette.

FIGS. 22A-22D illustrate an exemplary console 700 that includes a drawer like door 701, with FIG. 22A showing door 701 in an open configuration. Exemplary cassette 705 is shown in a position about to be placed downward into contact with door 701. As shown, cassette 705 (as well as any cassette in FIGS. 22A-22D) may include any number of fluid pathway tubing sections to facilitate flow therethrough. Console 700 is shown to include one or more functional features generally shown as 702, which may include any of the features herein including a bubble detector, pressure sensor head (with rollers), part of a pressure sensing system (e.g. a load cell), and one or more linear actuators that are adapted to individually control the flow of fluid through the one or more fluid tubing pathways. Any aspect of any console herein may be incorporated or implemented into the consoles in FIGS. 22A-22D. In FIG. 22A, door 70 is shown slid out and open, allowing cassette to be placed downward and into contact with door 701 in the compartment shown in FIG. 22B. Door 701 may then be slid shut and closed with the cassette engaged with the console inside, as shown in FIG. 22C. To subsequently open door 701 for cassette 705 removal, a mechanical door actuator 703 may be depressed, which may be adapted to release a locking mechanism and open door 701, as shown in FIG. 22D.

Figures 23A, 23B, 23C, 23D:
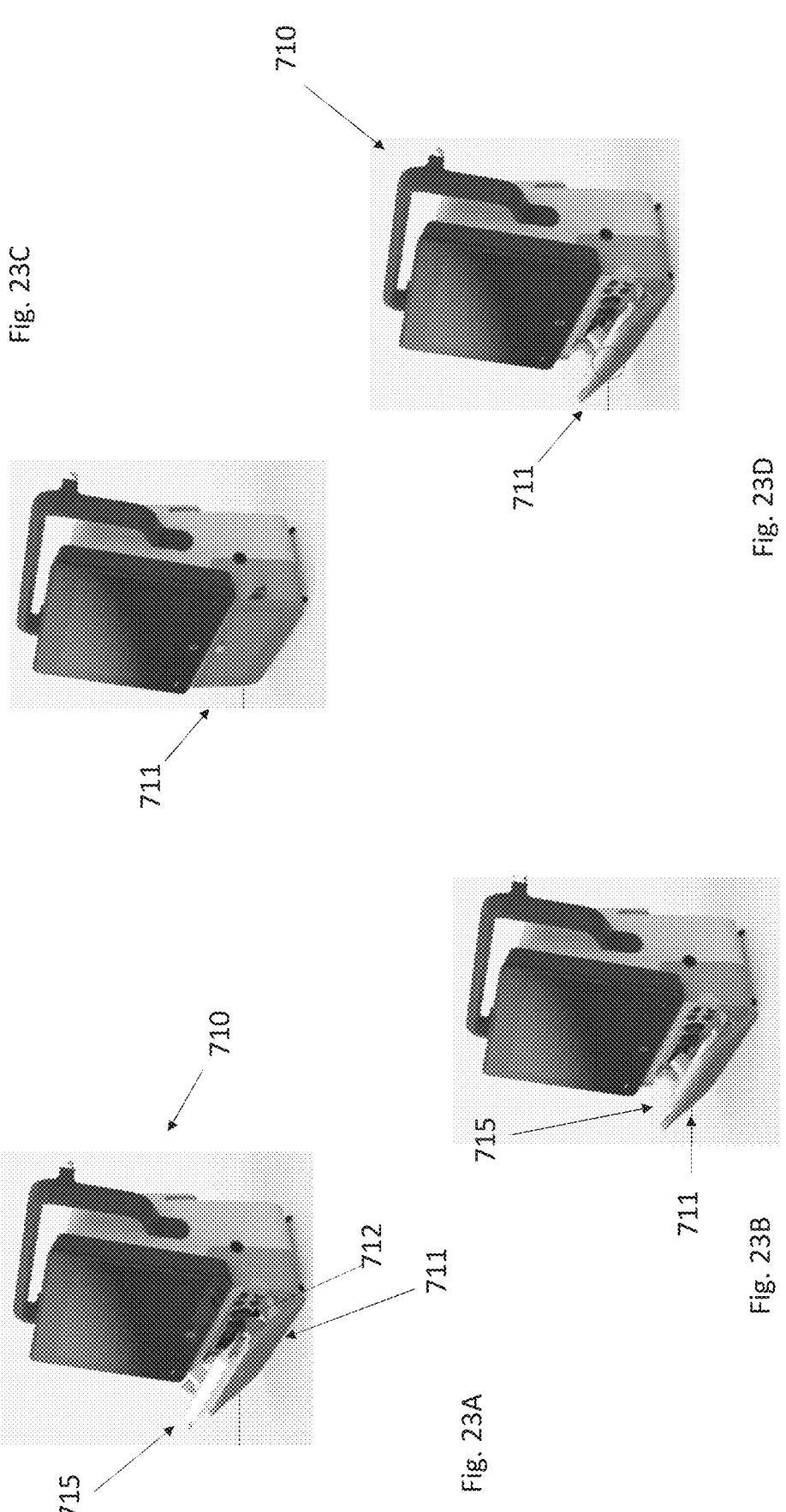
FIGS. 23A, 23B, 23C, and 23D illustrate an exemplary external console and an exemplary fluid cassette.

FIGS. 23A-23D illustrate an exemplary console 710 and cassette 715, which may have features that are labeled similarly to similar FIGS. 22A-22D. One difference between door 711 and door 701 is that door 711 opens in a hinge-like manner, as shown in FIG. 23A. Cassette 715 can then be slid into the compartment as shown in FIG. 23B. Door 711 can then be closed with cassette 715 engaged with the console, as shown in FIG. 23C. To subsequently open door 711 for cassette 715 removal, a mechanical door actuator may be depressed, which may be adapted to release a locking mechanism and open door 711, as shown in FIG. 22D.

Figures 24A, 24B, 24C, 24D:
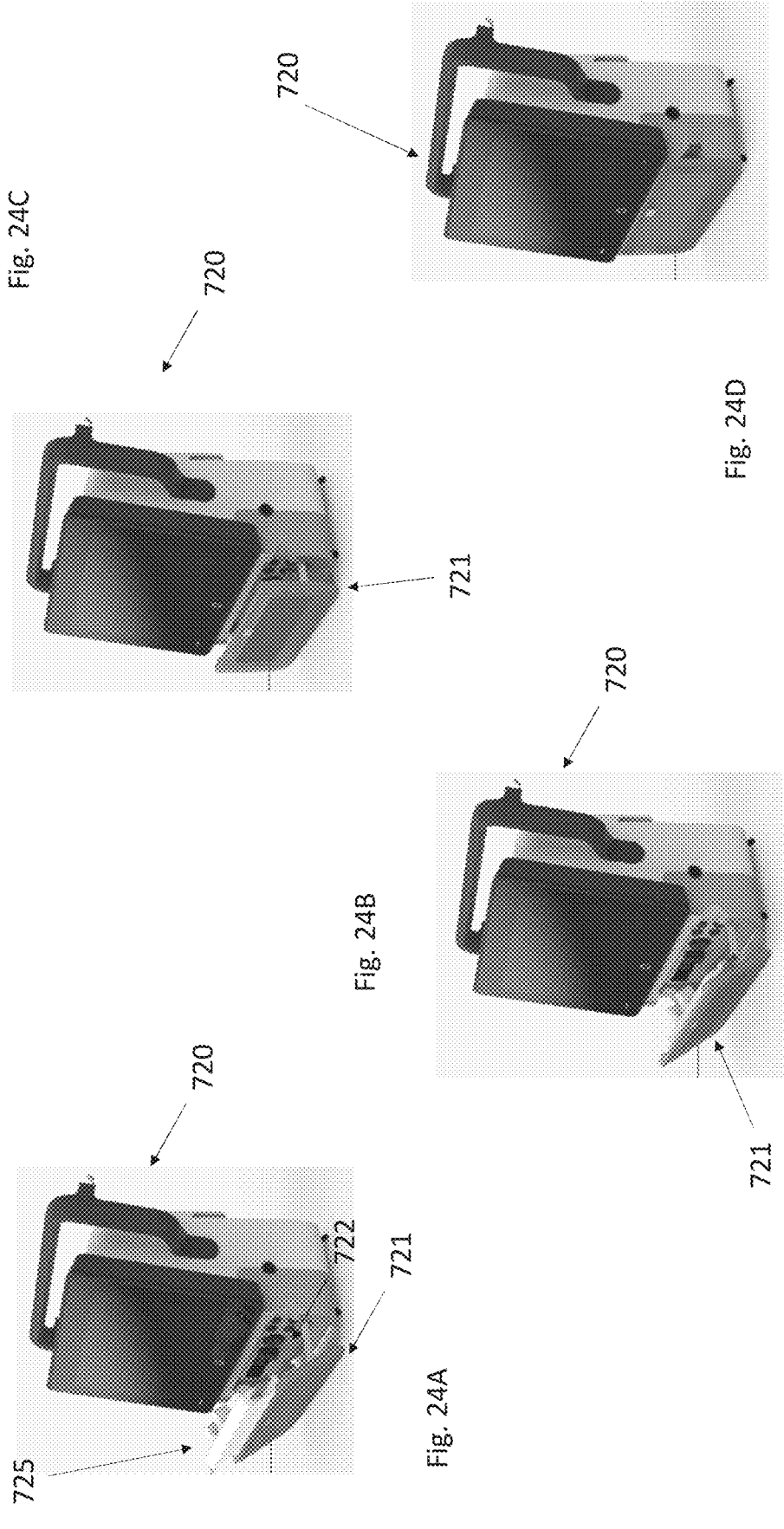
FIGS. 24A, 24B, 24C, and 24D illustrate an exemplary external console and an exemplary fluid cassette.

FIGS. 24A-24D illustrate an exemplary console 720 and cassette 725, which may have features that are labeled similarly to similar FIGS. 22A-22D and FIGS. 23A-23D, and which may incorporate any features herein. As shown in FIG. 24A, door 721 in this example both slides and hinges out to reveal the internal compartment. The cassette (e.g., cassette 725) is inserted into the compartment, as shown in FIG. 24B. The door is closed to an upright or vertical configuration as shown in FIG. 24C (which at this state is similar to the drawer door above in 22A-22C), and door 721 is then pushed inward directly toward the console, to the closed position as shown in FIG. 24D. The design in FIGS. 24A-24D may be considered a hybrid door design to the designs in FIGS. 22A-D (drawer) and FIGS. 23A-D (hinge). To subsequently open door 721 for cassette 725 removal, a mechanical door actuator may be depressed, which may be adapted to release a locking mechanism and open door 721.

FIGS. 25A-25D illustrate an alternative design in which console functional components (pump head, linear actuators) may be above and/or below the cassette as the cassette 735 is slid into a slot 731 in the console 730. Console door 732 is slid upward (or downward in alternative designs) in this example prior to cassette positioning, which is shown in FIG. 25A. Once cassette 735 is slid into slot 731 as shown in FIG. 25B, door 732 can then be closed by moving it down to cover the cassette, as shown in FIG. 25C. The cassette may be removed after sliding door 732 upward, as shown in FIG. 25D.

What is claimed is:

1. A removable cassette for use with an external console to facilitate and control the flow of fluid through an intravascular blood pump, comprising:

a cassette housing comprising a pump head receiving area sized and configured to receive a pump head therein; and a clean fluid pathway between a fluid inlet and a fluid outlet;

a second clean fluid pathway in communication with the fluid inlet and a second fluid outlet, wherein the clean fluid pathway and the second clean fluid pathway are the same pathway between the inlet and a pathway bifurcation in the cassette;

the cassette housing having a first side with a flow control opening formed therein, the flow control opening positioned relative to the clean fluid pathway so as to provide access to the clean fluid pathway from the first side through the flow control opening, the flow control opening sized and configured to receive therein a flow controller of an external console to facilitate the control of fluid through the clean fluid pathway.

2. The cassette of claim 1, the cassette housing first side further comprising a second flow control opening formed therein, the second flow control opening positioned relative to the second clean fluid pathway so as to provide access to the second clean fluid pathway from the first side through the second flow control opening, the second flow control opening sized and configured to receive therein a second flow controller of an external console to facilitate the control of fluid through the second clean fluid pathway.

3. The cassette of claim 2, further comprising a waste fluid pathway in between a waste fluid inlet and a waste fluid outlet.

4. The cassette of claim 3, the cassette housing first side further comprising a waste flow control opening formed therein, the waste flow control opening positioned relative to the waste fluid pathway so as to provide access to the waste fluid pathway from the first side through the waste flow control opening, the waste flow control opening sized and configured to receive therein a third flow controller of the external console to facilitate the control of fluid through the waste fluid pathway.

5. The cassette of claim 1, wherein the bifurcation comprises at least part of a pressure sensor.

6. The cassette of claim 5, wherein the bifurcation a deformable membrane or diaphragm.

7. The cassette of claim 1, wherein the bifurcation comprises a pressure sensor housing in fluid communication with the clean fluid pathway.

8. The cassette of claim 1, wherein the fluid outlet and the second fluid outlet are on a second side of the cassette housing, the second side being orthogonal to the first side.

9. The cassette of claim 8, wherein the fluid inlet is on a third side of the cassette housing that is spaced from the second side of the cassette housing.

10. The cassette of claim 8, further comprising a waste fluid inlet on the second side of the cassette housing.

11. The cassette of claim 10, further comprising a waste fluid outlet on the second side of the cassette housing.

12. The cassette of claim 1, wherein the flow control opening extends through an external side of the cassette housing so that a backstop of a console can interface with an external side surface of the clean fluid pathway to facilitate compressing the clean fluid pathway.

13. The cassette of claim 1, wherein the cassette housing comprises a unitary housing body.

14. The cassette of claim 1, wherein the cassette housing comprises a body comprises a plurality of components.

15. The cassette of claim 14, wherein the cassette housing comprises an internal subassembly comprising the clean fluid pathway, the cassette housing further comprising one or more shells disposed about the internal assembly.

16. The cassette of claim 1, wherein the cassette is sized and configured to be secured to an external console to facilitate fluid movement through the fluid pathway when a pump console is activated.

\* \* \* \* \*